United States Patent
Vaquero et al.

(10) Patent No.: US 7,422,604 B2
(45) Date of Patent: Sep. 9, 2008

(54) PRELOADED IOL INJECTOR

(75) Inventors: Edward Vaquero, Fairport, NY (US); Brian D. Rathert, St. Petersburg, FL (US); Thomas M. Heyman, Placentia, CA (US); Aaron M. Torp, Rochester, NY (US); Martin P. Schooping, Hamlin, NY (US); Philip L. Bryan, Honeoye Falls, NY (US); William J. Seyboth, Rochester, NY (US); George Clark, Rochester, NY (US); Robert J. Egan, Livonia, NY (US); Jon P. Cullen, Churchville, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 592 days.

(21) Appl. No.: 10/813,862

(22) Filed: Mar. 31, 2004

(65) Prior Publication Data

US 2005/0049606 A1 Mar. 3, 2005

Related U.S. Application Data

(63) Continuation-in-part of application No. 10/651,785, filed on Aug. 28, 2003.

(51) Int. Cl.
*A61F 9/00* (2006.01)
(52) U.S. Cl. .................................. 623/6.12
(58) Field of Classification Search ............ None
See application file for complete search history.

(56) References Cited

U.S. PATENT DOCUMENTS

| 4,787,904 A | 11/1988 | Severin et al. |
| 5,066,297 A | 11/1991 | Cumming et al. |
| 5,139,501 A | 8/1992 | Klaas et al. |

(Continued)

FOREIGN PATENT DOCUMENTS

EP 1338254 A 8/2003

(Continued)

OTHER PUBLICATIONS

PCT/US2004/027003, "International Preliminary Report on Patentability," (Dec. 30, 2005).

*Primary Examiner*—Corrine McDermott
*Assistant Examiner*—Christopher Daniel Prone
(74) *Attorney, Agent, or Firm*—Jeffrey B. Powers

(57) ABSTRACT

A preloaded intraocular lens injection device includes a retainer for releasably holding an IOL in an unstressed state. The retainer and IOL are removably attached to an injector body and are sealed in the same package for delivery to a surgeon. In an alternate embodiment, the retainer and IOL are coupled together and sealed in one package and the injector body is sealed in a separate package with the surgeon attaching the retainer to the injector body at the time of surgery. To deliver the IOL through the injector body, the retainer is removed from the injector body causing the IOL to release from the retainer and become located in an unstressed state in the injector body. A compressor is moved to the closed position to compress the IOL, the injector tip is inserted through a small incision in an eye and a plunger is advanced to push the IOL through and out the injector body tip and into an eye.

15 Claims, 25 Drawing Sheets

U.S. PATENT DOCUMENTS

| | | | |
|---|---|---|---|
| 5,304,182 A | 4/1994 | Rheinish et al. |
| 5,468,246 A | 11/1995 | Blake |
| 5,578,042 A | 11/1996 | Cumming |
| 5,643,275 A | 7/1997 | Blake |
| 5,728,102 A | 3/1998 | Feingold et al. |
| 6,048,347 A | 4/2000 | Erdman |
| 6,280,449 B1 | 8/2001 | Blake |
| 6,312,433 B1 | 11/2001 | Butts et al. |
| 6,406,481 B2 | 6/2002 | Feingold et al. |
| 6,468,282 B2 * | 10/2002 | Kikuchi et al. | 606/107 |
| 6,491,697 B1 | 12/2002 | Clark et al. |
| 6,497,708 B1 | 12/2002 | Cumming |
| 6,500,181 B1 | 12/2002 | Portney |
| 6,503,275 B1 * | 1/2003 | Cumming | 623/6.12 |
| 6,537,283 B2 | 3/2003 | Van Noy |
| 6,558,395 B2 | 5/2003 | Hjertman et al. |
| 6,607,537 B1 | 8/2003 | Binder |
| 2001/0007942 A1 | 7/2001 | Kikuchi et al. |
| 2002/0082609 A1 | 6/2002 | Green |
| 2002/0151904 A1 | 10/2002 | Feingold et al. |

FOREIGN PATENT DOCUMENTS

| | | |
|---|---|---|
| WO | WO 01/64147 A1 | 9/2001 |
| WO | WO 03/045285 A | 6/2003 |
| WO | WO 2004/010903 A | 2/2004 |
| WO | WO 2004/010903 A1 | 2/2004 |

* cited by examiner

PRELOADED IOL INJECTOR

RELATED APPLICATION

This application is a continuation-in-part of application Ser. No. 10/651,785 filed Aug. 28, 2003.

BACKGROUND OF THE INVENTION

The present invention relates to ophthalmic surgical devices and methods. More particularly, the present invention relates to a device and method for inserting an intraocular lens (IOL) into an eye and wherein the IOL may be conveniently preloaded in and packaged together with the injector device.

IOLs are artificial lenses used to replace the natural crystalline lens of the eye when the natural lens has cataracts or is otherwise diseased. IOLs are also sometimes implanted into an eye to correct refractive errors of the eye in which case the natural lens may remain in the eye together with the implanted IOL. The IOL may be placed in either the posterior chamber or anterior chamber of the eye. IOLs come in a variety of configurations and materials. Some common IOL styles include the so-called open-looped haptics which include the three-piece type having an optic and two haptics attached to and extending from the optic; the one-piece type wherein the optic and haptics are integrally formed (e.g., by machining the optic and haptics together from a single block of material); and also the closed looped haptic IOLs. Yet a further style of IOL is called the plate haptic type wherein the haptics are configured as a flat plate extending from opposite sides of the optic. The IOL may be made from a variety of materials or combination of materials such as PMMA, silicone, hydrogels and silicone hydrogels, etc.

Various instruments and methods for implanting the IOL in the eye are known. In one method, the surgeon simply uses surgical forceps having opposing blades which are used to grasp the IOL and insert it through the incision into the eye. While this method is still practiced today, more and more surgeons are using more sophisticated IOL inserter devices which offer advantages such as affording the surgeon more control when inserting the IOL into the eye. IOL inserter devices have recently been developed with reduced diameter insertion tips which allow for a much smaller incision to be made in the cornea than is possible using forceps alone. Smaller incision sizes (e.g., less than about 3 mm) are preferred over larger incisions (e.g., about 3.2 to 5+mm) since smaller incisions have been attributed to reduced post-surgical healing time and complications such as induced astigmatism.

Since IOLs are very small and delicate articles of manufacture, great care must be taken in their handling. In order for the IOL to fit through the smaller incisions, they need to be folded and/or compressed prior to entering the eye wherein they will assume their original unfolded/uncompressed shape. The IOL inserter device must therefore be designed in such a way as to permit the easy passage of the IOL through the device and into the eye, yet at the same time not damage the delicate IOL in any way. Should the IOL be damaged during delivery into the eye, the surgeon will most likely need to extract the damaged IOL from the eye and replace it with a new IOL, a highly undesirable surgical outcome.

Thus, as explained above, the IOL inserter device must be designed to permit easy passage of the IOL therethrough. It is equally important that the IOL be expelled from the tip of the IOL inserter device and into the eye in a predictable orientation and manner. Should the IOL be expelled from the tip too quickly or in the wrong orientation, the surgeon must further manipulate the IOL in the eye which could result in trauma to the surrounding tissues of the eye. It is therefore highly desirable to have an inserter device which allows for precise loading of the IOL into the inserter device and which will pass and expel the IOL from the inserter device tip and into the eye in a controlled, predictable and repeatable manner.

To ensure controlled expression of the IOL through the tip of the IOL inserter device, the IOL must first be loaded into the IOL inserter device. The loading of the IOL into the inserter device is therefore a precise and very important step in the process. Incorrect loading of an IOL into the inserter device is oftentimes cited as the reason for a failed IOL delivery sequence. Many IOL injector devices on the market today require the IOL to be loaded into the injector at the time of surgery by the attending nurse and/or surgeon. Due to the delicate nature of the IOL, there is a risk that the nurse and/or surgeon will inadvertently damage the IOL and/or incorrectly load the IOL into the injector device resulting in a failed implantation. Direct handling and/or loading of the IOL into the injector by the nurse and/or surgeon is therefore undesirable.

In a typical IOL inserter device, the IOL inserter utilizes a plunger having a tip which engages the IOL (which has been previously loaded and compressed into the inserter lumen) to pass it through the inserter lumen. The IOL thus interfaces with the plunger tip as well as the lumen of the inserter device. The lumen typically is dimensioned with a narrowing toward the open tip thereof in order to further compress the IOL as it is advanced through the lumen. The tip of the lumen is sized for insertion through the surgical incision which, as stated above, is presently preferred in the sub 3 mm range. Thus, an inserter lumen will typically be dimensioned larger at the load area of the IOL and gradually decrease in diameter to the tip of the lumen where the IOL is expressed into the eye. It will be appreciated that the compressed diameter of the IOL at the lumen tip is the same as the inner diameter of the lumen tip, preferably sub 3 mm as stated above. Each of these component interfaces are dynamic in the sense that the forces acting between the interfacing components (i.e., the IOL, the plunger tip and the inserter lumen) will vary as the IOL is pushed through the lumen. Control of these dynamic forces is therefore of utmost importance or otherwise the IOL may be damaged during delivery due to excessive compressive forces acting thereon. For example, as the IOL is advanced by the plunger through an ever-decreasing diameter lumen, the IOL is being compressed while at the same time the forces necessary to push the IOL through the lumen increase. This may lead to excessive force between the plunger tip and the IOL resulting in possible damage to the IOL and/or uncontrolled release of the IOL from the lumen tip. Also, the force of the plunger tip may cause the IOL to twist and/or turn as it is moved through the inserter whereby the force between the IOL and the plunger tip and/or the inserter lumen may uncontrollably increase to the point of IOL damage.

Various inserter devices have been proposed which attempt to address these problems, yet there remains a need for an IOL inserter and method which removes the need for direct handling of the IOL by the nurse and/or surgeon and which generally simplifies operation of the IOL injector device and IOL delivery process.

SUMMARY OF THE INVENTION

In a first aspect of the invention, an injector device is provided having an IOL preloaded therein and wherein the injector device and IOL are packaged together as a single unit. The IOL is releasably held by an IOL retainer in a "preloaded" position in the unstressed state; i.e., in a state where substantially no stress acts upon the optic portion thereof. In this embodiment, the device is in the preloaded position from the time of final assembly and packaging at the manufacturing site, through shipping and actual use of the device by a surgeon. The storage position is thus the position of the IOL while it is held by the IOL retainer.

The injector body includes an opening and IOL loading bay wherein the retainer removably attaches to the inserter body with the IOL captured by the retainer and held thereby in the preloaded position. The IOL retainer includes features for releasably supporting the IOL optic. In IOLs which include one or more haptics attached to and extending from the optic periphery, the IOL retainer further includes features for releasably supporting the haptic(s) as well as the optic. In the preferred embodiment, the haptics are supported by the IOL retainer in the preloaded position at the correct vault angle (i.e., the angle at which they normally extend from the optic periphery).

At manufacturing, the IOL is releasably coupled to the IOL retainer with the optic and haptics held by IOL support elements of the retainer. The retainer is then removably attached to the inserter body at the opening and loading bay thereof. A stripper element extends between the IOL optic and retainer body to prevent the IOL from remaining coupled to the retainer when the retainer is removed from the inserter body. This will be explained more fully below.

Once the device is ready to be used, the package is opened in a sterile field of the surgical room and viscoelastic, as required, is applied about the IOL and/or injector body according to the desires of the surgeon and/or directions for use provided with the packaging. The IOL retainer is then detached from the injector device. This may be done by manually pulling the IOL retainer apart from the injector device. In this regard, a finger pull or other feature is provided on the body of the IOL retainer to facilitate manual decoupling of the retainer from the injector body.

As stated above, a stripper element is provided between the retainer and IOL optic. As such, as the retainer is pulled away from the injector body, the IOL optic presses against the stripper element which thereby prevents the IOL from staying with the retainer as the retainer is decoupled from the injector body. Thus, the movement of the retainer as it is being decoupled from the injector device causes the IOL optic to press against the stripper element and then release from the optic support element of the IOL retainer, in addition to the IOL haptic(s) releasing from the haptic support elements of the IOL retainer. Once fully released from the retainer, the IOL is in the "loaded" position within the injector device and is ready to be compressed and delivered through a small incision into an eye.

In an alternate embodiment of the invention, the retainer and IOL attached thereto may be packaged separately from the injector device whereby the retainer and IOL are attached to the injector body at the time of surgery rather than at the time of manufacture.

The injector includes means for compressing, rolling or otherwise forcing the IOL into a smaller cross-section for delivery through the injector. In a preferred embodiment of the invention, the injector device includes a compressor which extends laterally of the IOL loading bay of the injector body. The compressor is movable between fully open and fully closed positions and is in the open position when the injector device is packaged and the IOL is in the storage position. Once the package has been opened and the IOL retainer has been decoupled from the injector device, the compressor is moved to the closed position which compresses the IOL optic. A plunger is advanced at the proximal end of the injector device causing the tip of the plunger to engage the proximal end of the compressed optic. As the plunger is advanced further, the IOL is pushed through the distal end of the injector body and expressed into the eye in the intended manner.

In yet a further preferred embodiment of the invention, a haptic puller is provided at the distal end of the injector body which includes a finger for engaging the leading haptic of the IOL. Prior to fully advancing the plunger, the haptic puller is manually pulled away from the distal tip of the injector device causing the finger portion thereof to pull the leading haptic and straighten it within the distal tip of the injector device. This eliminates the possibility of the leading haptic becoming jammed inside the injector body as the plunger is being fully advanced through the injector device.

The relative positioning of the IOL retainer, the IOL and the injector device is such that upon decoupling the IOL retainer from the injector device (and thus release of the IOL from the retainer), the IOL becomes preferentially positioned inside the injector device. The IOL thus becomes positioned in a particular orientation inside the injector device relative to the plunger tip and haptic puller. This "IOL release position" results in the leading haptic correctly engaging the haptic puller, and the trailing haptic extending rearwardly of the plunger tip so that upon advancement of the plunger, the plunger tip will engage the IOL optic in the intended manner without obstruction or jamming of the trailing haptic.

DETAILED DESCRIPTION

Figure 1:
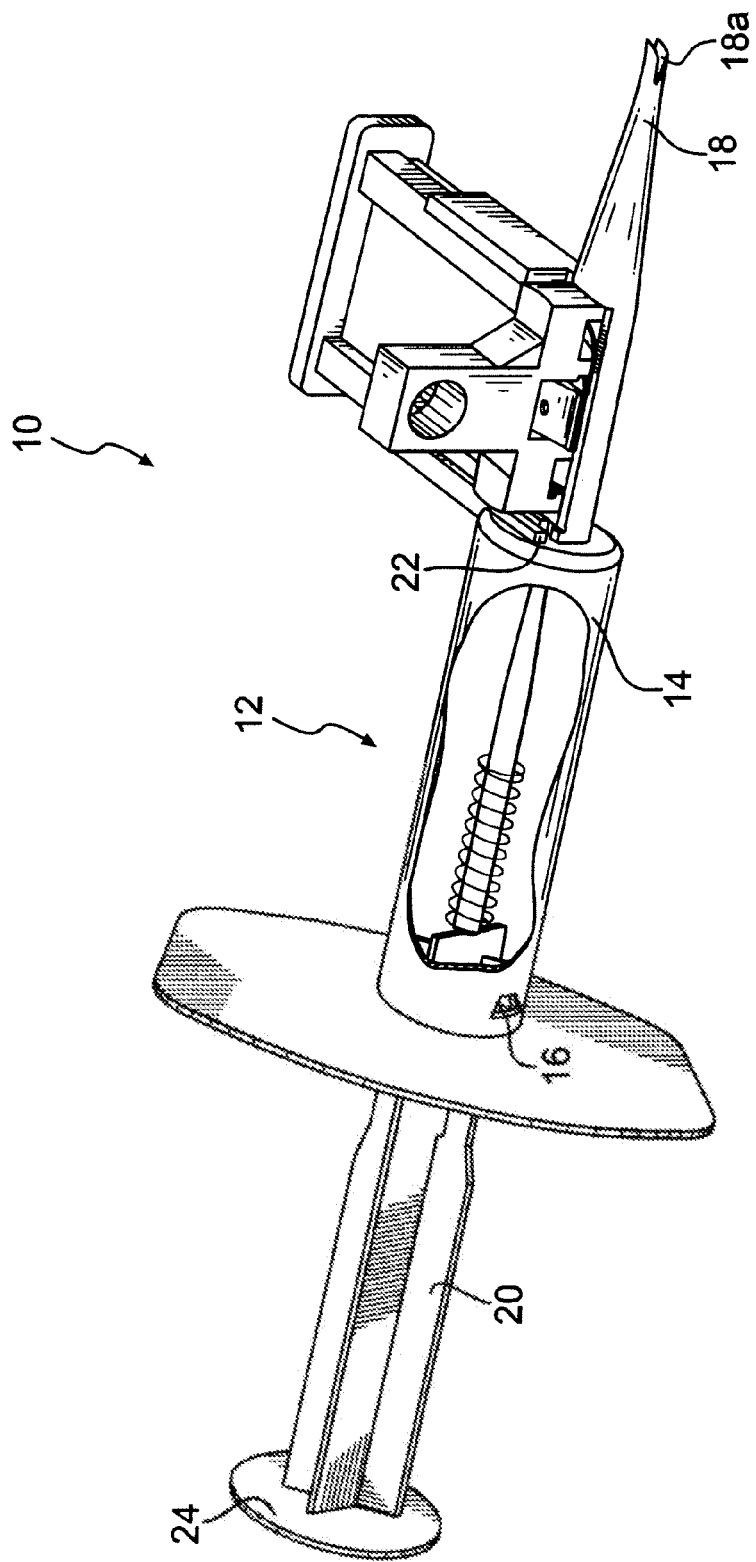
FIG. 1 is a perspective view of an embodiment of the invention showing the device with the retainer and IOL coupled to the injector body in the storage position.

Referring now to the drawing, there is seen in the Figures a preferred embodiment of the invention denoted generally by the reference numeral 10. In a first, broad aspect, the invention comprises a preloaded injector device for injecting an IOL into an eye. The term "preloaded" as used herein means that the injector body 12 is packaged together with an IOL wherein the IOL 30 is held by a retainer 40 in a storage position on the injector body (see also FIGS. 11 and 12). In an alternate embodiment of the invention, the injector device is "partially preloaded" meaning that the IOL 30 and retainer 40 are coupled and packaged together but not yet coupled to the injector body 12 (see also FIG. 10). In this alternate embodiment, the doctor or nurse attaches the retainer and IOL to the injector body at the time of surgery.

The injector body 12 includes a longitudinal lumen 14 extending from the proximal end 16 to distal end 18 thereof. The lumen may assume any desired cross-sectional shape although circular or oval shapes are preferred. The lumen 14 tapers inwardly toward distal tip 18 so that the IOL 30 is gradually compressed to a very small cross-section as it exits tip 18a. Tip 18a may include one or more longitudinally extending slits 18a' to permit a gradual expansion of the IOL 30 as it exits the tip 18a within the eye. This prevents uncontrolled expansion of the IOL in the eye which could potentially damage the delicate surrounding tissues of the eye. Proximal end 16 may include a finger hold flange 17 preferably configured with a straight edge 17a as shown for resting device 10 on a flat surface. A plunger 20 having distal and proximal lengths 20a, 20b, respectively, and a distal plunger tip 22 (see FIG. 2) and proximal thumb press 24 telescopes within lumen 14 for engaging and pushing the IOL 30 through lumen 14 and out of distal tip 18a. The IOL delivery sequence will be explained in more detail below. It is understood that the overall configuration of the injector body 12 may vary from that shown and described herein. It is furthermore understood that the components of the injector device may be made of any suitable material (e.g., polypropylene) and may be wholly or partly opaque, transparent or translucent to better visualize the IOL within the injector device and the IOL delivery sequence.

Injector body 12 further includes an opening 26 which opens into lumen 14. Opening 26 is configured to accept an IOL 30 therein for delivery of the IOL out distal tip 18a. Discussion will now be turned to the IOL Preloaded Position followed by discussion of the IOL Load and Delivery Sequence.

The IOL Preloaded Condition

Figure 5A:
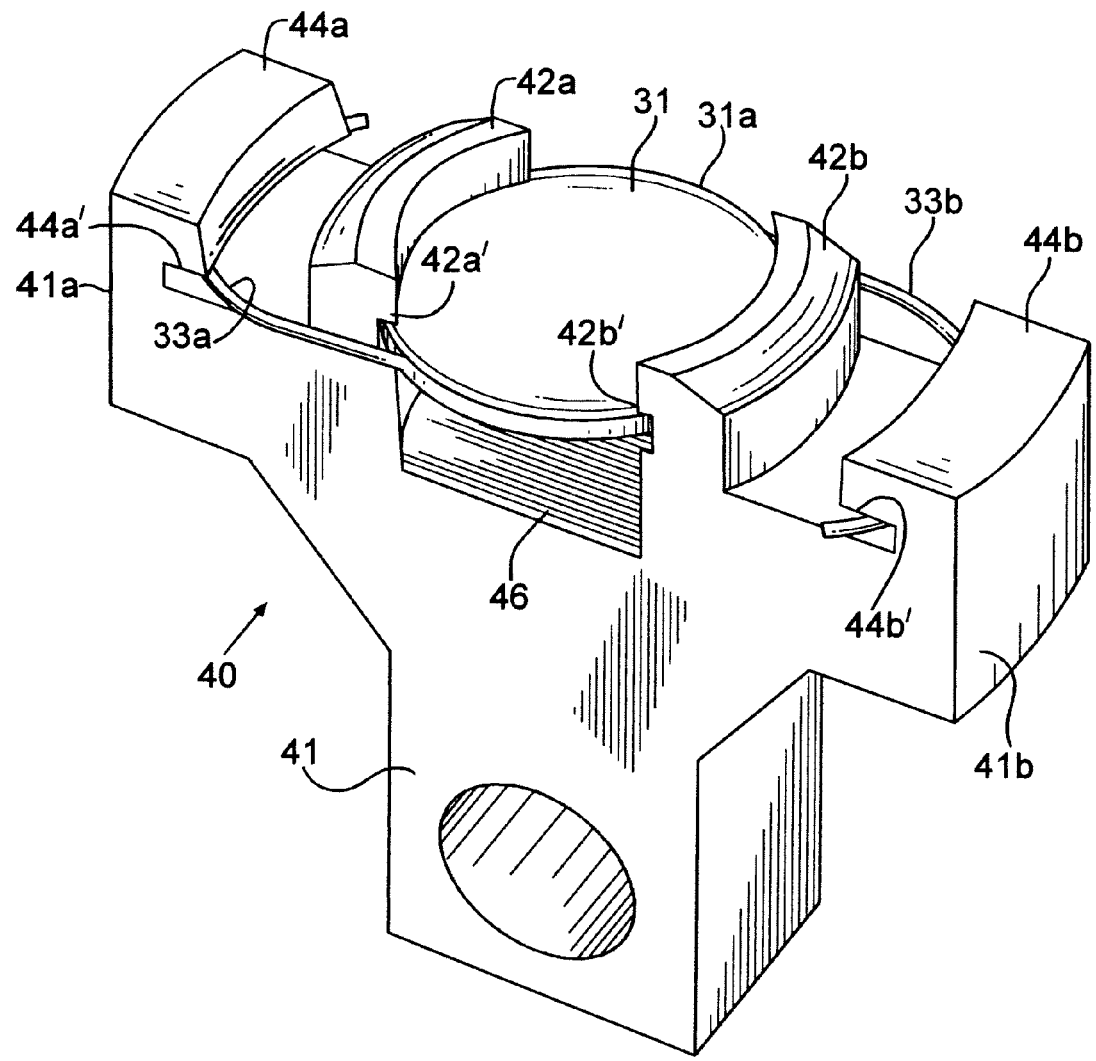
FIGS. 5A-5C are perspective, top and side views of the IOL retainer with an IOL releasably held thereby.
Figure 5B:
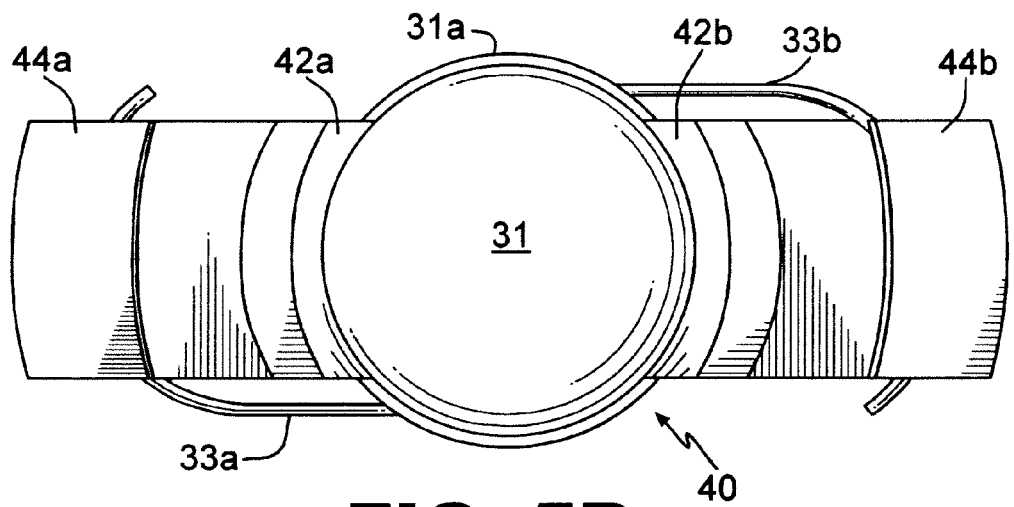
Figure 5C:
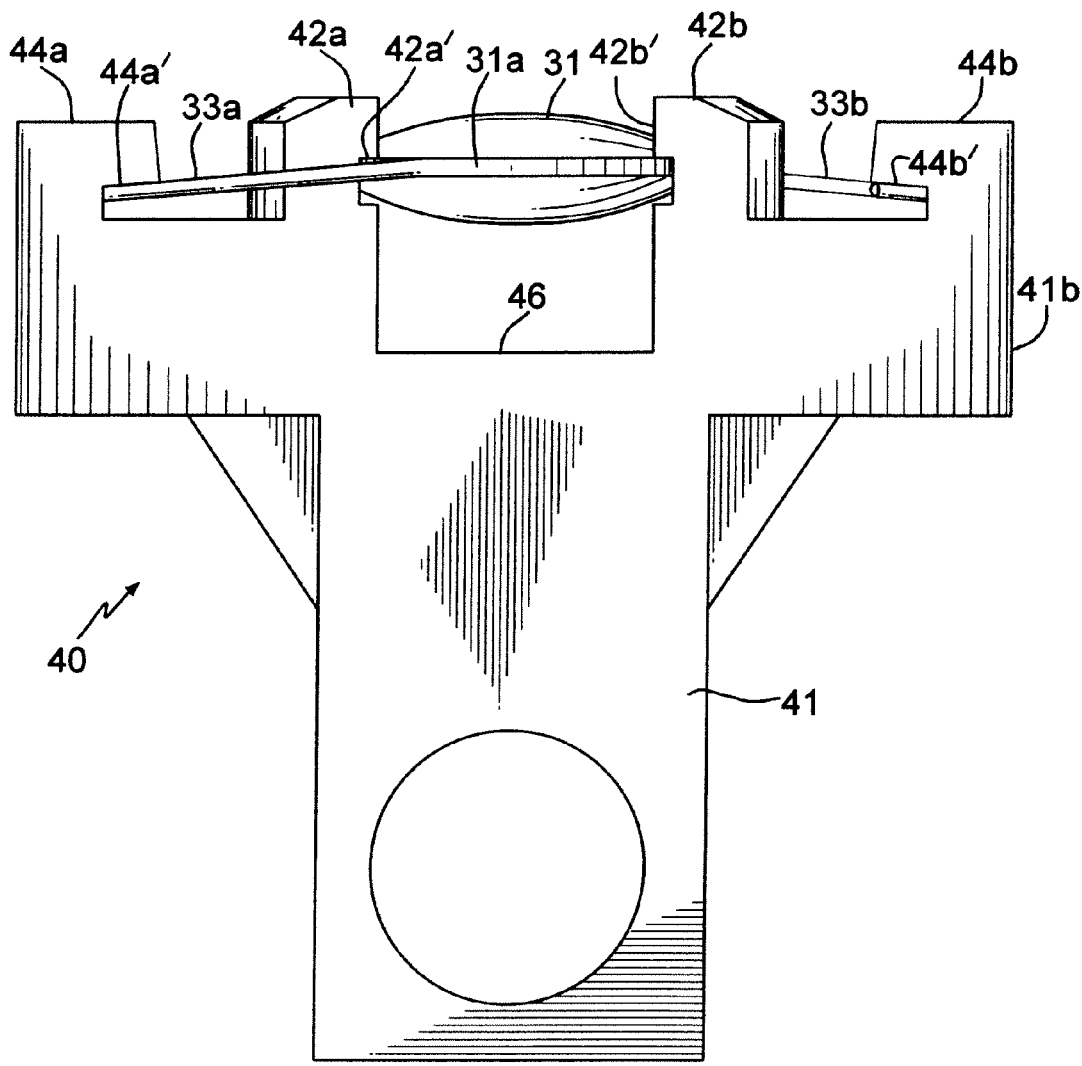

In a preferred embodiment, device 10 includes an IOL retainer 40 used for releasably holding an IOL 30 in the preloaded position relative to injector body 12. The IOL retainer 40, with IOL 30 releasably held thereby, is removably attached to the injector body 14 at opening 26. As seen best in FIGS. 5A-C, IOL retainer 40 includes one or more, but preferably two optic support elements 42a and 42b each having a lip 42a', 42b' or other feature for releasably supporting the IOL optic 31 at the periphery 31a thereof. Alternatively or in addition to the optic support elements, one or more, but preferably two haptic support elements 44a and 44b are provided on retainer 40, each of which include a finger 44a', 44b' or other feature for releasably supporting one or more, but preferably two haptics 33a and 33b which attach to and extend from the optic 31. In this regard, it is understood that the IOL configuration shown and described herein is for discussion purposes only, and that the present invention is not to be limited thereby. The invention may be easily adapted to IOLs of any configuration and type (e.g., IOLs with plate, open or closed loop haptics, anterior chamber IOLs, posterior chamber IOLs, accommodating IOLs (including single and double lens types), etc.). The overall configuration of the IOL retainer 40 may thus likewise vary so as to be cooperatively configured with and releasably hold the particular IOL configuration being used with the device. In all embodiments, the retainer 40 holds at least the IOL optic 31 in the unstressed state. It is furthermore preferable that retainer 40 hold the IOL haptics at the correct vault angle (i.e., the angle from which they normally extend from the IOL optic periphery). It is even furthermore preferable that the haptic support elements maintain loop haptics at the correct angle of curvature. In FIGS. 5A-C, it is seen that the haptic support elements constrain the haptics along the outer curved edges thereof. This ensures that the haptic curvature, which is designed and set at manufacture of the haptics, does not increase or bend out of specification during storage of the IOL and retainer.

At manufacture, the IOL 30 is releasably secured to the IOL retainer 40. This may be done by engaging the IOL optic 31 with the IOL supporting elements 42a, 42b, and/or engaging the haptics 33a, 33b with the haptic supporting elements 44a, 44b, respectively. For purposes of description, haptic 33a will be referred to as the leading haptic since it becomes located distally in the injector body while haptic 33b will be referred to as the trailing haptic since it becomes located proximally in the injector body (see FIG. 2).

Releasably attaching the IOL 30 to the IOL retainer 40 may be done by a worker using a pair of tweezers, for example, although other methods may be used as desired, including automated or semi-automated means.

Figure 11:
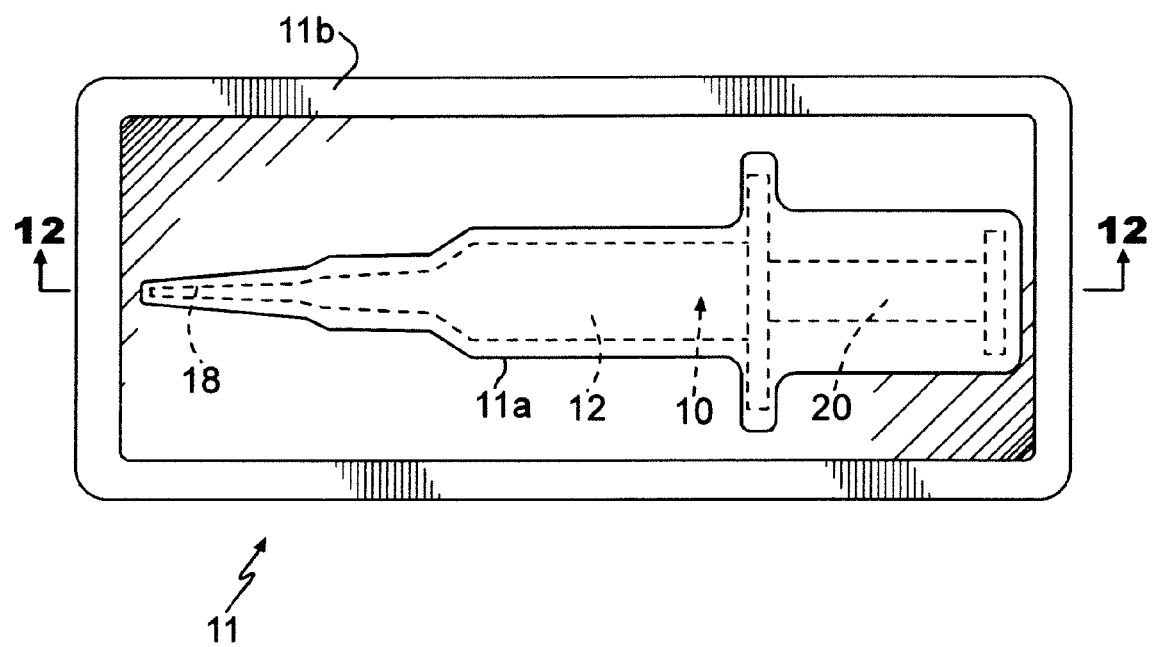
FIG. 11 is a plan view of the preloaded embodiment of the invention showing the injector body 12, retainer 40 and IOL 30 coupled together and sealed in a single package.
Figure 12:
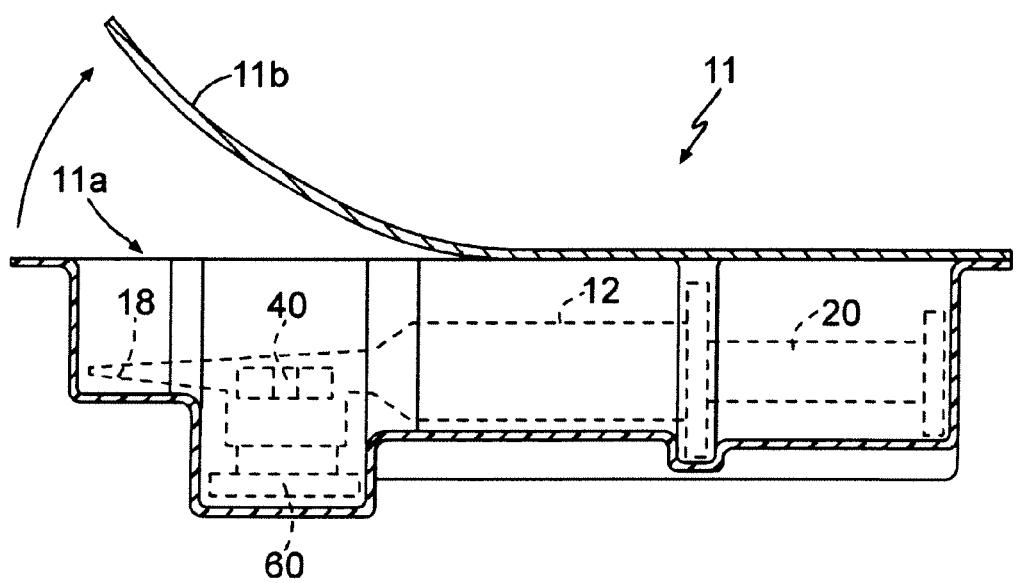
FIG. 12 is a cross-sectional view of the package of FIG. 11 as taken generally along the line 12-12 in FIG. 11.

As discussed above, in the preloaded embodiment of the invention, the retainer 40 and IOL 30 are coupled to the injector body 12 at manufacturing and sealed and sterilized in the same package for delivery to the surgeon. For example, as seen in FIGS. 11 and 12, a plastic package 11 thermoformed to include a cavity 11a in the general shape of the injector device 10 is provided for packaging device 10 together with retainer 40 and IOL 30 coupled thereto. A flexible cover sheet 11b is sealed about the perimeter of cavity 11a to seal the package. At the time of surgery, the cover 11b is peeled back to access device 10.

Figure 3A:
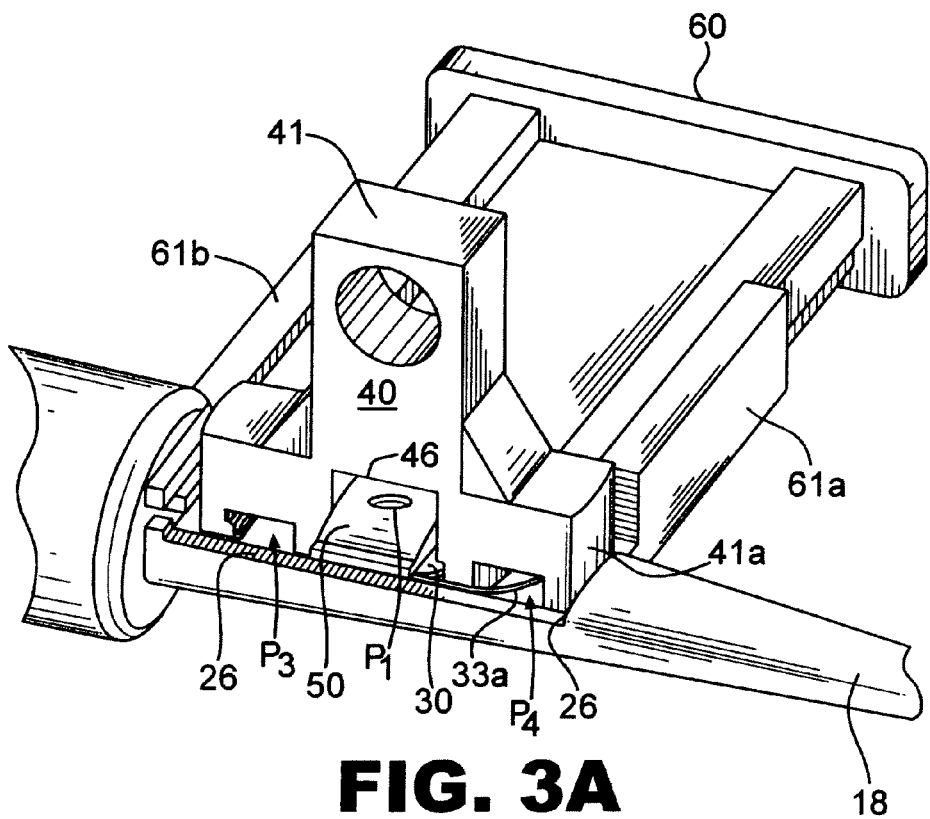
FIG. 3A is an enlarged perspective view of the loading bay area of the injector device of FIG. 1.

Thus, once the IOL 30 is releasably secured to retainer 40 as described above, IOL retainer 40 is removably attached to the injector body at opening 26. This may be done via suitable mechanical holding features which will removably connect the retainer 40 to the injector body 12, examples including friction fit, snap fit, interference fit, cooperative tabs and catches, deterits, etc. As seen in FIGS. 1 and 3A, retainer 40 is held in place at opening 26 via a friction fit between the surfaces defining opening 26 and the opposite outer wall surfaces 41a and 41b of retainer 40. It will be seen that when retainer 40 and IOL 30 are coupled together and attached to injector body 12, IOL optic 31 is unstressed and furthermore does not touch any part of the injector body 12. This ensures the delicate IOL optic 31 will not be damaged during storage.

Figure 3B:
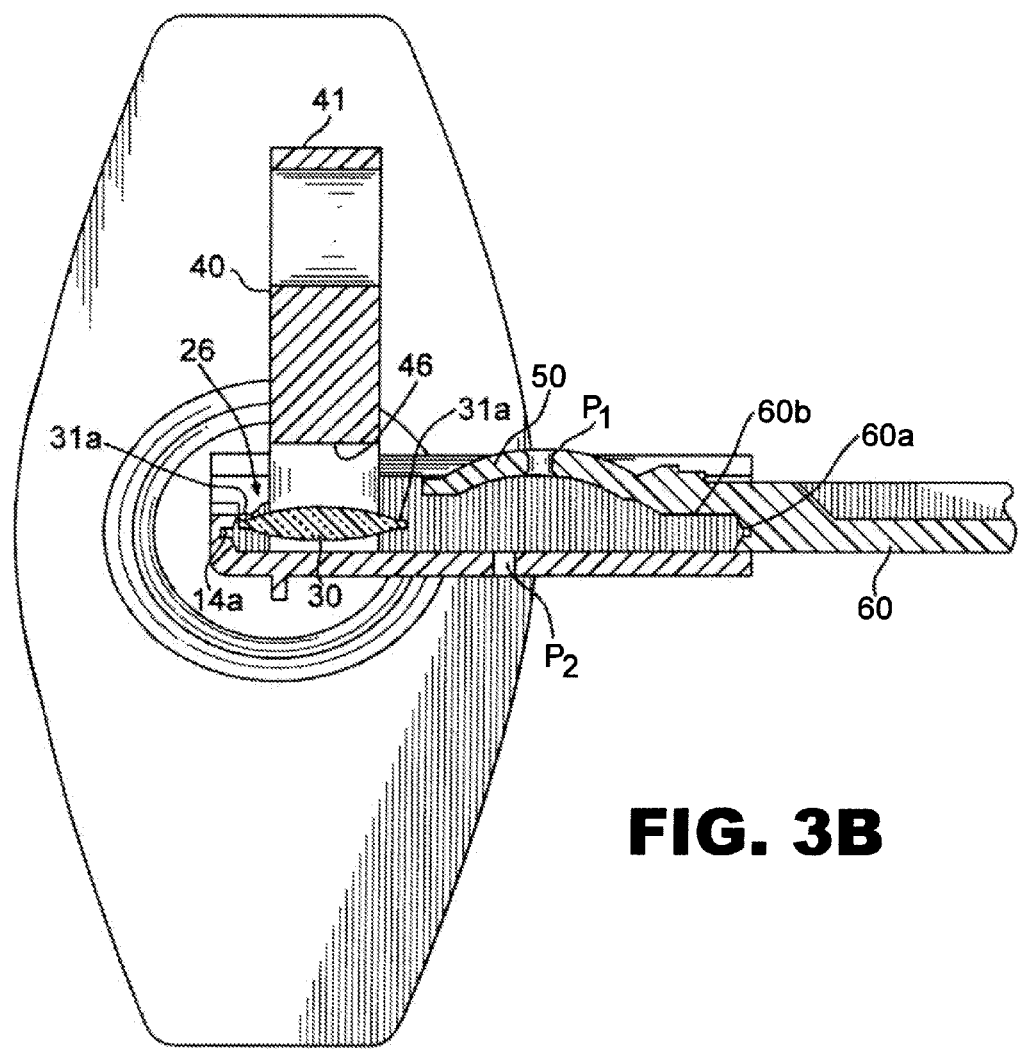
FIG. 3B is a cross-sectional view taken through the IOL loading bay of the injector device with the compressor drawer in the fully open position.
Figure 3C:
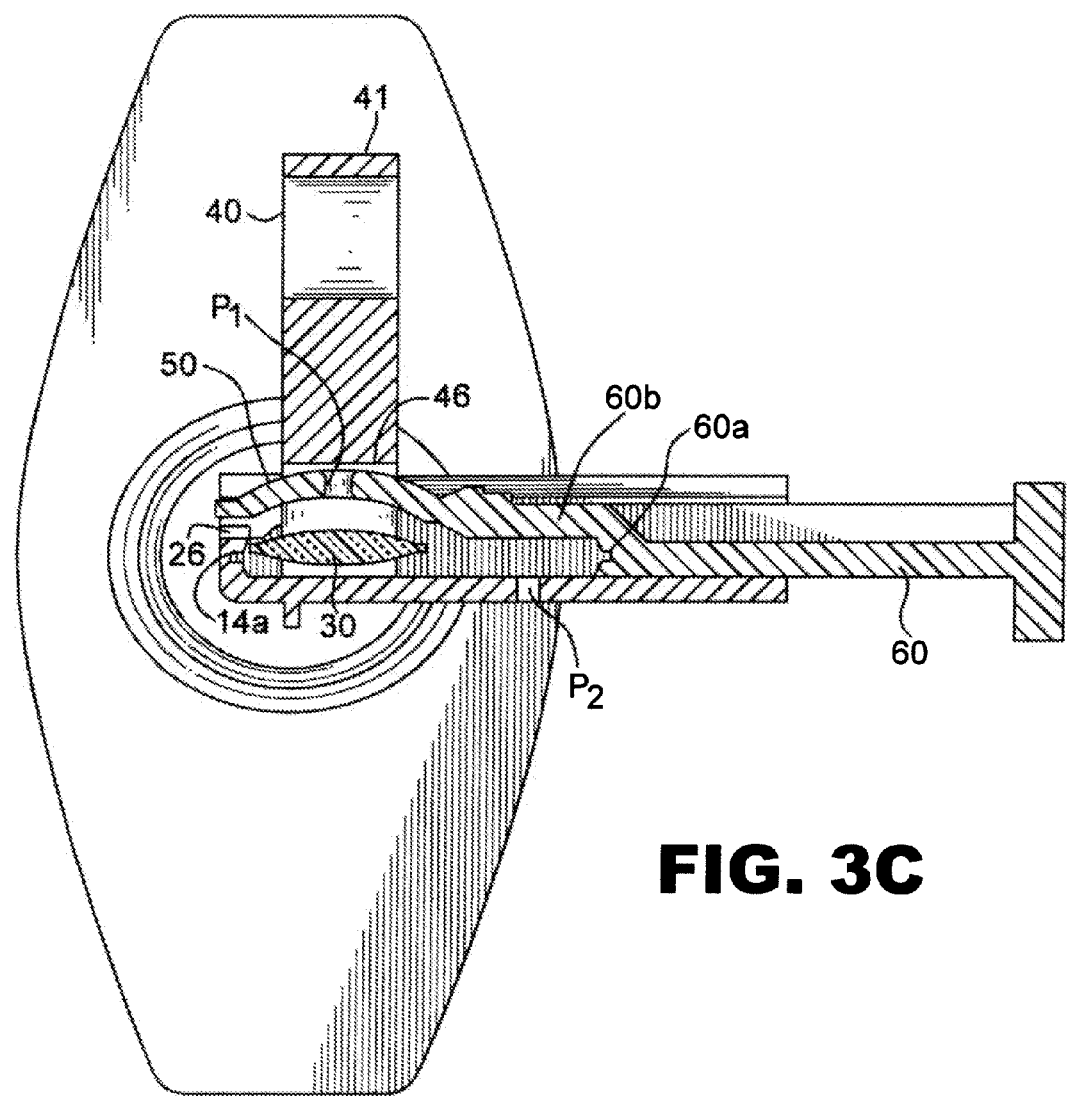
FIG. 3C is a cross-sectional view taken along the line 3C-3C of FIG. 3A.

When retainer 40 and IOL 30 are coupled together and attached to injector body 12, a stripper finger 50 is located between the IOL optic 31 and the center wall surface 46 of retainer 40 as seen best in FIGS. 1, 3A and 3C. The primary function of the stripper finger 50 is to prevent the IOL 30 from lifting with the retainer 40 when the retainer is detached from the injector body (this operation will be described below). In a preferred embodiment of the invention, the stripper finger 50 is attached to the compressor drawer 60 which is movable with respect to injector body 12 between a fully open position as seen in FIG. 3B, a mid-way position seen in FIGS. 1, 3A, 3C and 3E, and the fully closed position seen in FIGS. 3D, 4, 6 and 7. The stripper finger 50 is located between the IOL optic 31 and center wall surface 46 when the compressor 60 is in the mid-way position, which is also the preloaded position of the injector device as described herein. When the compressor drawer 60 is moved to the fully closed position, the stripper finger 50 moves therewith and comes to rest in a position laterally adjacent the injector body 12 as seen in FIGS. 3D, 4, 6 and 7.

Figure 3D:
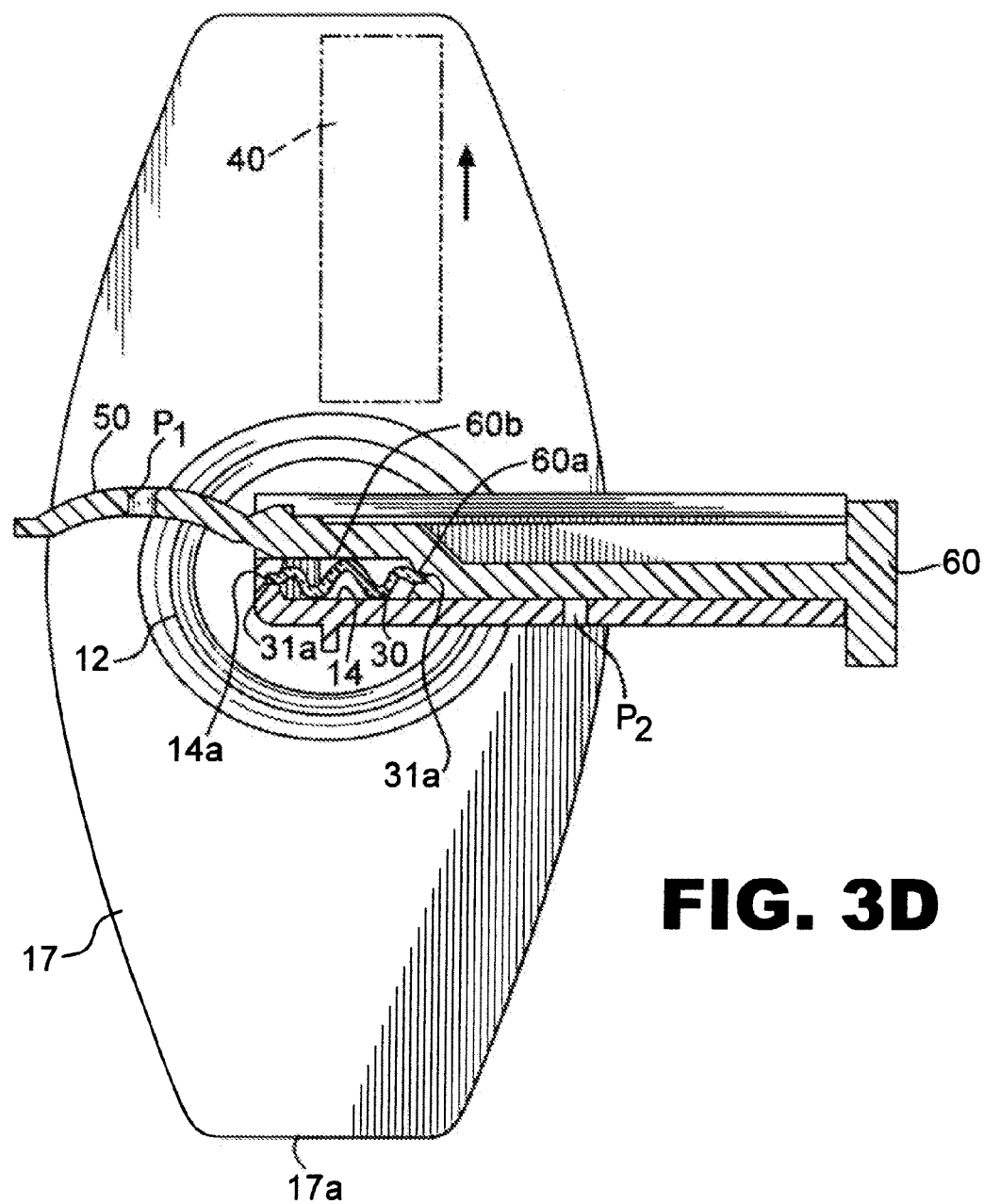
FIG. 3D is the view of FIG. 3C with the compressor drawer shown in the fully closed position.
Figure 3E:
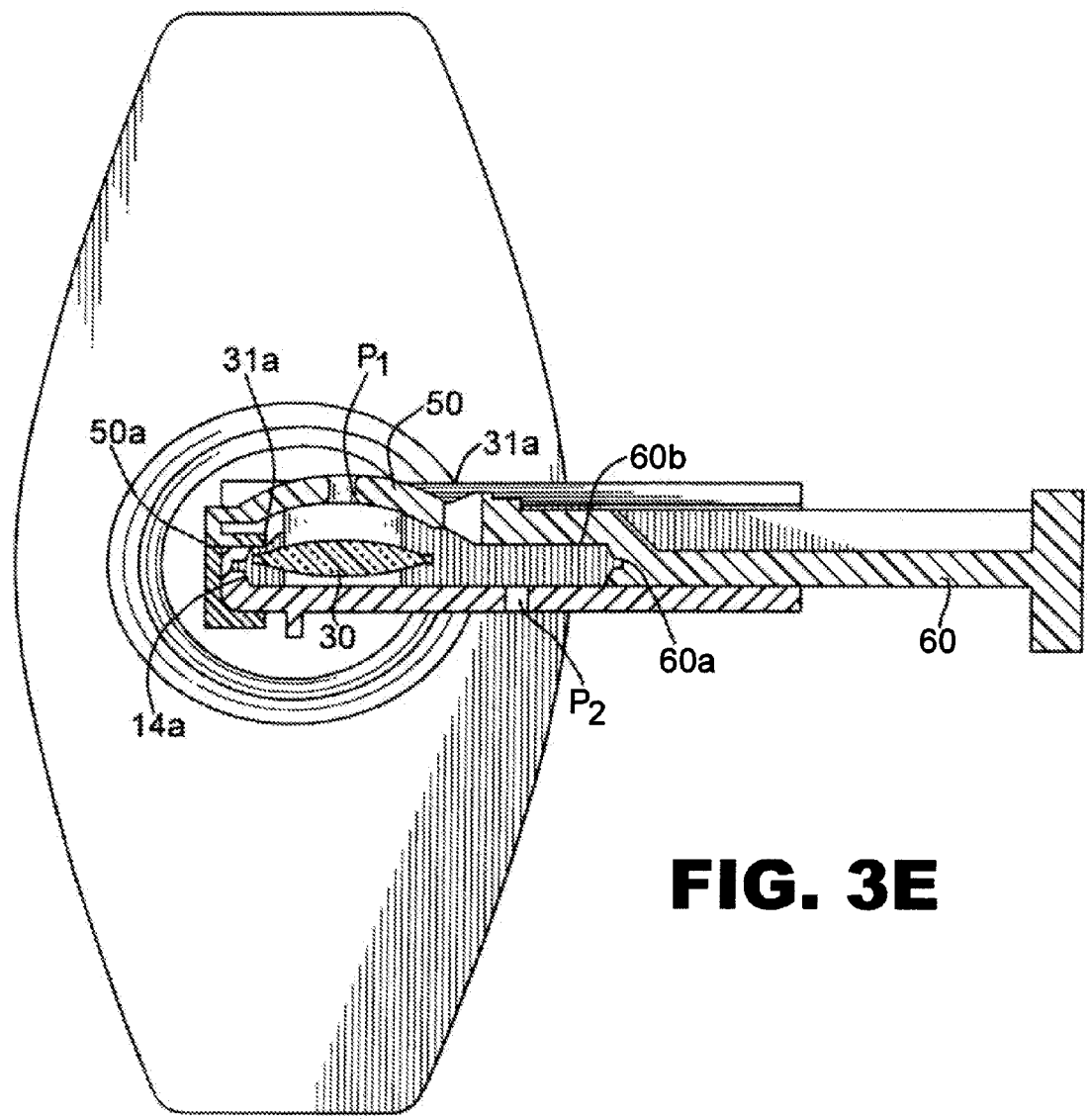
FIG. 3E is a cross-sectional view taken through the IOL loading bay area and showing an alternate embodiment of the stripper finger component of the injection device.
Figure 4:
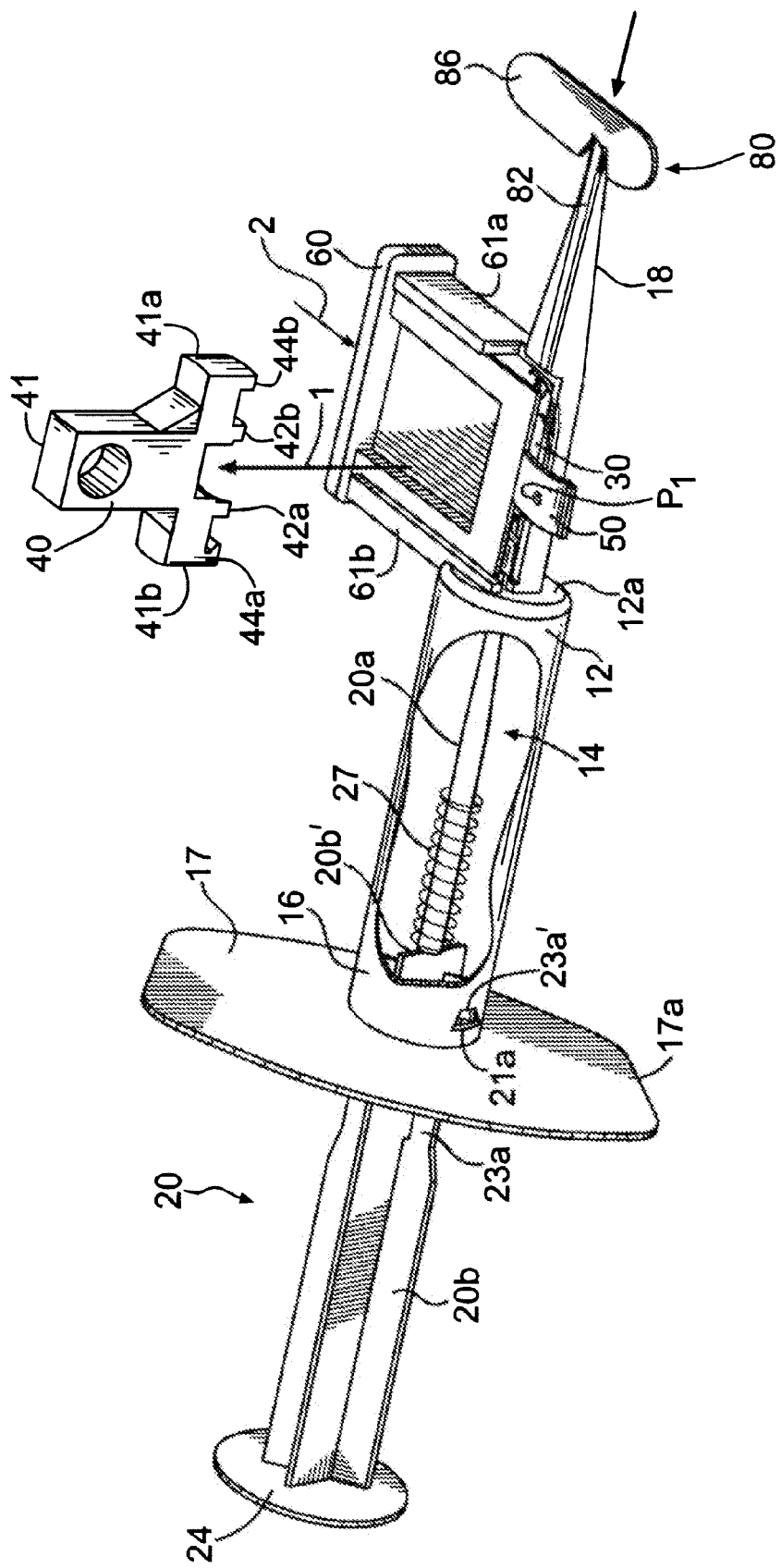
FIG. 4 is the view of FIG. 1 showing removal of the IOL retainer from the injector body and the compressor drawer in the fully closed position.

In an alternate embodiment, the stripper finger 50 may be formed separate from the compressor drawer 60 if desired. One such example is seen in FIG. 3E where the stripper finger 50 is formed with a clip 50a which may be mounted to injector body 12 opposite to and separately of compressor drawer 60. In this embodiment, the stripper finger 50 is removed from the injector body 12 after removal of retainer 40 and prior to closing the compressor drawer 60. Other embodiments will be apparent to those skilled in the art for stripping the IOL 30 from the retainer 40 as the retainer is removed from the injector body 12 and are thus within the scope of this invention.

Referring to FIGS. 1, 2, 4, 6 and 7, it is seen that the plunger 20 includes distal and proximal plunger shaft lengths 20a, 20b, respectively, having a plunger tip 22 at the distal end thereof and a thumb press 24 at the proximal end thereof for manually operating the injector device. The plunger tip 22 is configured for engaging the IOL optic 31 at the periphery 31a thereof as the plunger 20 is advanced toward the distal tip 18a of the injector body 12. It is very important that the plunger tip 22 not damage the IOL optic 31. The plunger tip 22 is thus designed to prevent damage to the IOL optic 31. In the preferred embodiment, the tip is bifurcated into first and second tip portions 22a and 22b, whereby the IOL optic periphery 31a becomes engaged between tip portions 22a, 22b as seen in FIG. 2B. It is understood that other plunger tip designs may be used with the present invention as desired. It is furthermore preferred that the plunger shaft is rotationally fixed within lumen 14 to prevent unexpected rotation of the shaft (and thus the tip 22) with the lumen 14. The plunger shaft may be rotationally fixed by forming the proximal shaft length 20b and lumen 14 non-circular in cross-section.

Figure 6:
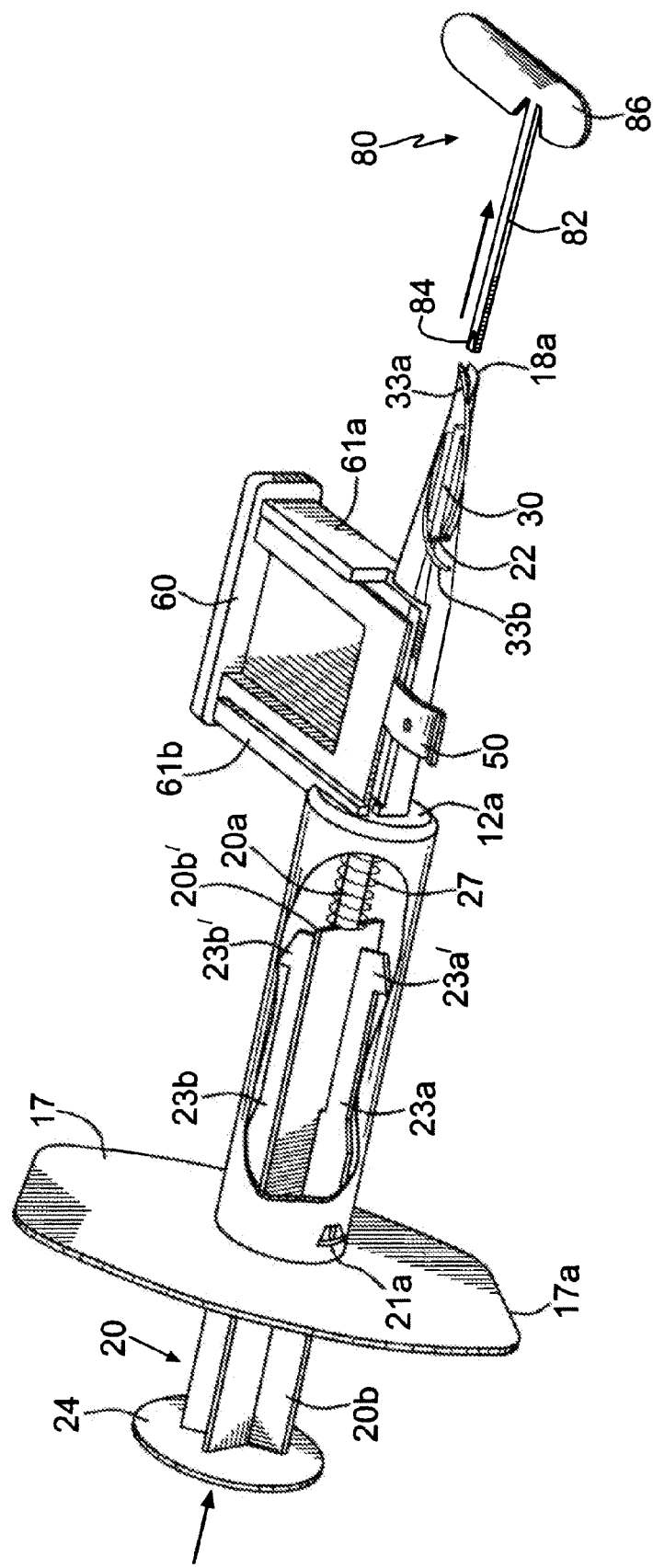
FIG. 6 is a perspective view showing the injector device in the process of ejecting an IOL therefrom.

In a particularly advantageous embodiment, the proximal length 20b of the plunger shaft is provided with one or more elongated fingers 23a, 23b forming springs which are biased radially outwardly against the interior wall of lumen 14 (see FIGS. 1 and 6). The purpose of spring fingers 23a, 23b is to provide proper centering of the plunger shaft and tip, as well as tactile resistance between the plunger 20 and the lumen 14 as the plunger 20 is advanced therethrough. In the storage position, the plunger 20 is retracted to the position shown in FIG. 1. To ensure the plunger is not unintentionally dislodged from the injector body or unintentionally advanced within lumen 14, the free ends 23a' and 23b' are located within respective openings 21a, 21b (opening 21b not shown) formed in the injector body 12 adjacent the proximal end 16 thereof. When it is time to use the device, the surgeon presses upon the thumb press 24 whereupon the free ends 23a', 23b', assisted by their slanting edge faces, disengage from respective openings 21a, 21b, allowing the plunger to be freely advanced in a controlled manner through lumen 14. The bias of the spring fingers 23a, 23b against the interior wall of the lumen 14 provides the surgeon with continuous tactile feedback allowing the surgeon to advance the plunger (and thus the IOL) through the lumen 14 in a very concise and controlled manner.

Figure 2A:
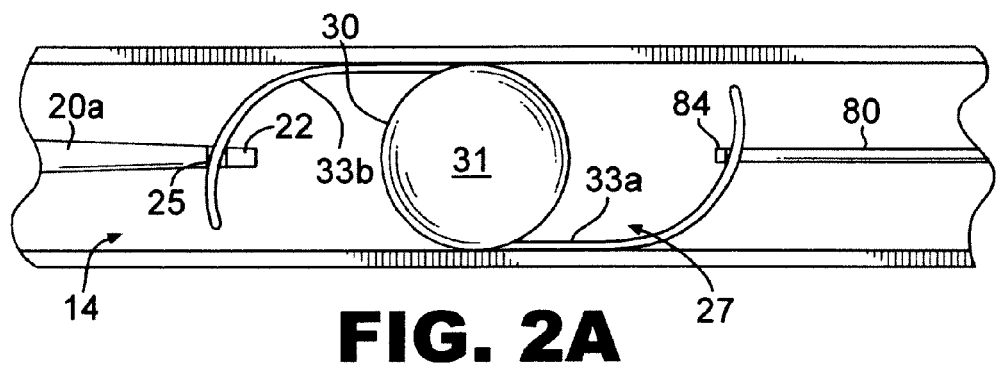
FIG. 2A is a partial plan view of the injector body showing the IOL loading bay portion thereof.
Figure 2B:
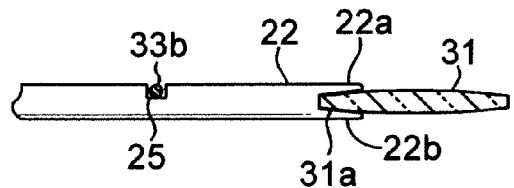
FIG. 2B is a partial side elevational view in section showing the trailing haptic residing in a recess located adjacent the plunger tip which is engaging the IOL optic.

Referring again to the plunger/IOL engagement, it is important that the IOL trailing haptic 33b not interfere with the plunger tip/optic engagement. In this regard, the end portion of the trailing haptic locates rearwardly of the plunger tip upon removal of retainer 40 and release of IOL 30 therefrom. In a preferred embodiment, a recessed area 25 is provided rearwardly of tip 22 on plunger shaft length 20a (FIG. 2A). With the plunger 20 in the ready position seen in FIG. 1, the recessed area 25 of the plunger is generally aligned with the trailing haptic 33b of the IOL 30 held by retainer 40. As such, upon detaching retainer 40 from injector body 20, the trailing haptic 33b will release from the haptic support element 44b and fall into recessed area 25 of the plunger 20. Thus, as the plunger 20 is advanced during use of the device in surgery, the trailing haptic 33b will reside in recessed area 25 and not become entangled or otherwise interfere with the proper engagement of the plunger tip and IOL optic (FIG. 2B).

Referring to the leading haptic 33a, it is important that the leading haptic not become "bunched up" inside the continuously tapering injector tip 18 as the IOL 30 is being pushed therethrough. One way to prevent this from happening is to straighten the leading haptic 33a within tip 18. To accomplish this, a haptic puller 80 is provided which is the subject of commonly assigned U.S. Pat. No. 6,491,697, the entire disclosure of which is hereby incorporated by reference. Haptic puller 80 has a shaft 82, tip 84 and finger pull 86. At assembly, the tip 84 is inserted into the injector tip with the finger pull located outwardly adjacent thereto (see FIG. 4). The tip 84 is configured with a lip to engage the leading haptic 33a (see FIG. 2A). At the time of use of device 10, the haptic puller 80 is grasped at finger pull 86 and pulled away from the injector body 12 in the direction of the arrow in FIG. 6, thereby engaging and straightening the leading haptic 33a within tip 18, whereupon the haptic puller 80 may be discarded.

To ensure the leading haptic 33a becomes engaged with the haptic puller tip 84 when the IOL retainer 40 is removed from injector body 12, the haptic puller tip 84 is positioned in injector tip 18 in alignment with the leading haptic 33a as it is held by the haptic supporting element 44a of IOL retainer 40. Thus, upon detaching IOL retainer 40 from the injector body 12, the leading haptic 33a releases from the haptic supporting element 44a and falls into place on the haptic puller tip 84 as shown in FIG. 2A.

The IOL Loaded Condition and Delivery Sequence

Figure 8:
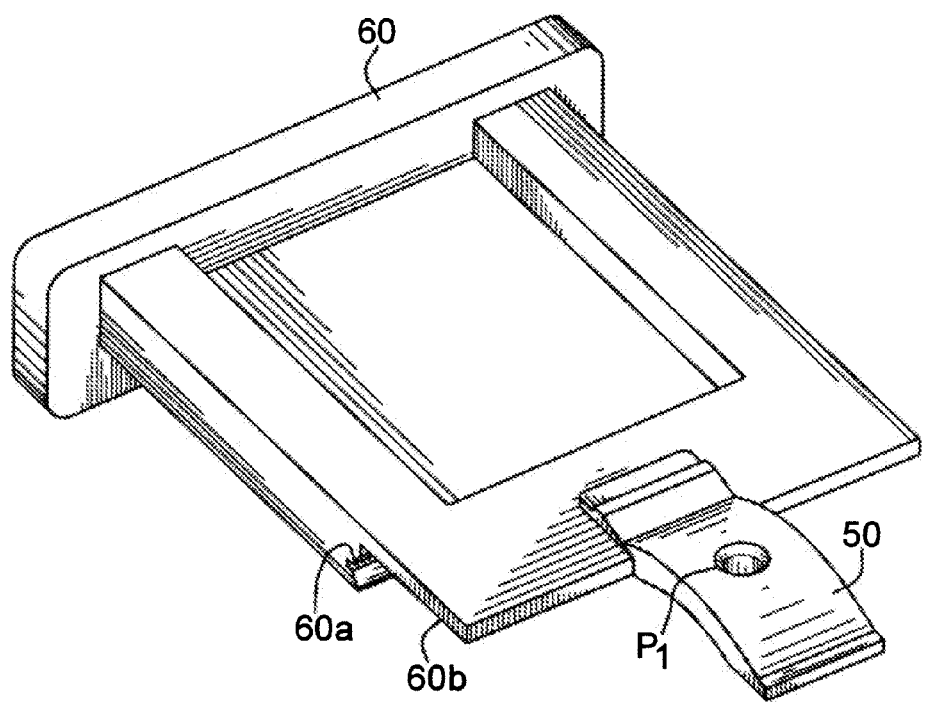
FIGS. 8 and 9 are perspective and plan views of the compressor drawer and stripper finger component of the injector device, respectively.
Figure 9:
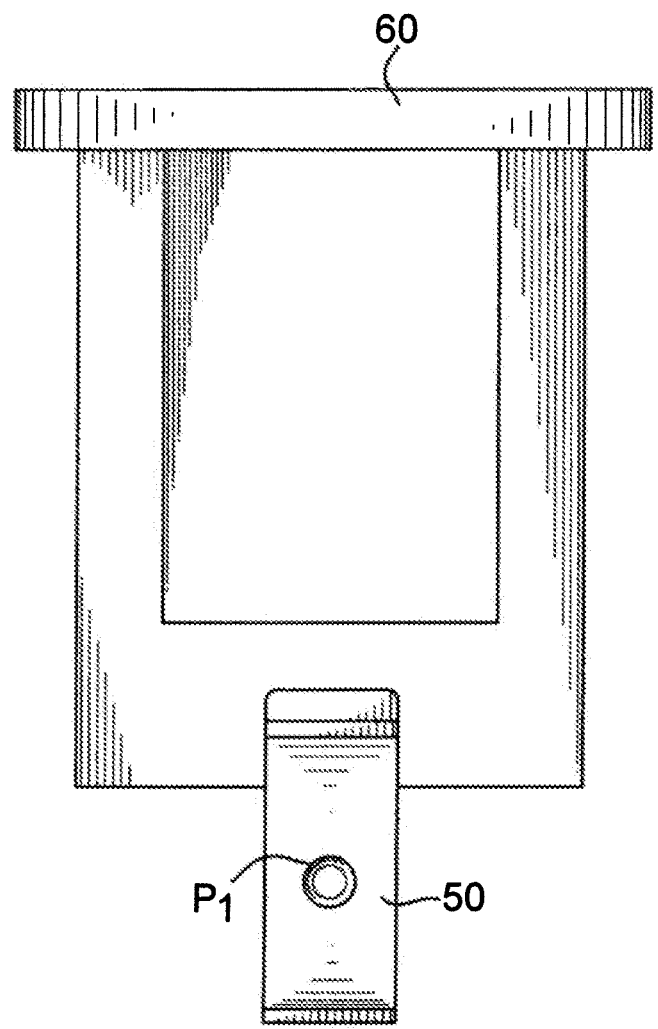

When it is time to use the injector device 10, the surgeon selects the injector device with the appropriate IOL preloaded therein as described above. The outer packaging is removed in a sterile field of the surgical suite. To load the IOL into the delivery position seen in FIG. 2A, the nurse or surgeon grasps and removes IOL retainer 40 from injector body 12. This is accomplished by manually grasping finger grip 41 and pulling the retainer 40 away from the injector body 12 as shown by directional arrow 1 in FIG. 4. As described above, the stripper finger 50 acts to prevent the IOL 30 from lifting together with retainer 40. Thus, the IOL optic 31 will release from the IOL optic support element 42a, 42b and the leading and trailing haptics 33a, 33b will release from their respective haptic support elements 44a, 44b. Once the retainer 40 has been fully detached from injector body 12, it may be discarded or recycled. With the IOL 30 thus fully released from retainer 40, the IOL optic 31 comes to rest in the loading bay area 27 of the injector lumen 14 with the leading haptic 33a engaging the haptic puller tip 84 and the trailing haptic 33b locating in the recessed area 25 adjacent the plunger tip 22 as described above. In this regard, it is noted that upon release of the IOL 30 from the retainer 40, IOL 30 will drop slightly in lumen 14. This is seen best in FIGS. 3C and 3D where in FIG. 3C, IOL 30 is held by retainer 40 with the optic periphery 31a located slightly above groove 14a which is formed in and extends longitudinally along the inside wall of lumen 14. Upon removal of retainer 40 and release of IOL 30 therefrom, the optic periphery 31a becomes aligned with groove 14a along one side of the lumen. Then, upon moving compressor drawer 60 to the fully closed position (see directional arrow 2 in FIG. 4), the opposite edge of the optic periphery 31a becomes engaged in groove 60a of drawer 60 (see also FIG. 8). Thus, lumen 14 together with lumen groove 14a, drawer groove 60a, and drawer top wall 60b compresses and encases IOL optic 31 within lumen 14. The locating of the optic periphery 31a inside opposite grooves 14a and 60a ensures a planar delivery of the IOL 30 through lumen 14 and out tip 18.

This manner of IOL planar delivery is described in more detail in commonly assigned U.S. Pat. No. 6,491,697 referred to above.

Prior to removing retainer 40, closing drawer 60 and compressing the IOL 30 inside the injector body, it may be desirable to apply viscoelastic to the area surrounding the IOL 30 to ease delivery of the IOL through the injector body. This is a common practice in the industry and the amount and location of viscoelastic application varies according to the instructions for use provided with the device as well as the desires of the surgeon. In any event, in a preferred embodiment, one or more viscoelastic access ports are provided on the injector device to facilitate application of the viscoelastic in the area of the IOL. One or more access ports $P_1$ may thus be provided in the form of a through-hole in stripper finger 50. The access port $P_1$ is accessible via an injection nozzle inserted into visco port $P_1$. Alternatively or in addition to access ports $P_1$, one or more access ports $P_2$ may be provided at any desired location through the wall of tip 18 (see FIGS. 3B-D). Alternatively or in addition to visco ports $P_1$ and $P_2$, visco may be applied in loading bay 27 at the openings $P_3$ and $P_4$ defined between the optic and haptic support elements of retainer 40 (see FIG. 3A). Once the viscoelastic has been applied as desired, retainer 40 is removed and the compressor drawer 60 is moved to the fully closed position whereupon the IOL optic 31 is compressed and ready for delivery through a small incision formed in an eye. The fully closed position of drawer 60 and compressed position of the IOL 30 is seen in FIG. 3D as described above. Drawer 60 is slidably received between cooperatively formed drawer slides 61a, 61b extending laterally from injector body 12 adjacent opening 26. Detents or other features (not shown) may be provided on the facing surfaces of drawer slides 61a, 61b and drawer 60 to assist in maintaining drawer 60 in the fully open and mid-way positions, respectively. Such drawer holding features are especially useful in preventing unintentional sliding and/or complete closing of drawer 60 prior to the time needed (e.g., during storage or opening of device 10 from its associated packaging).

Figure 7:
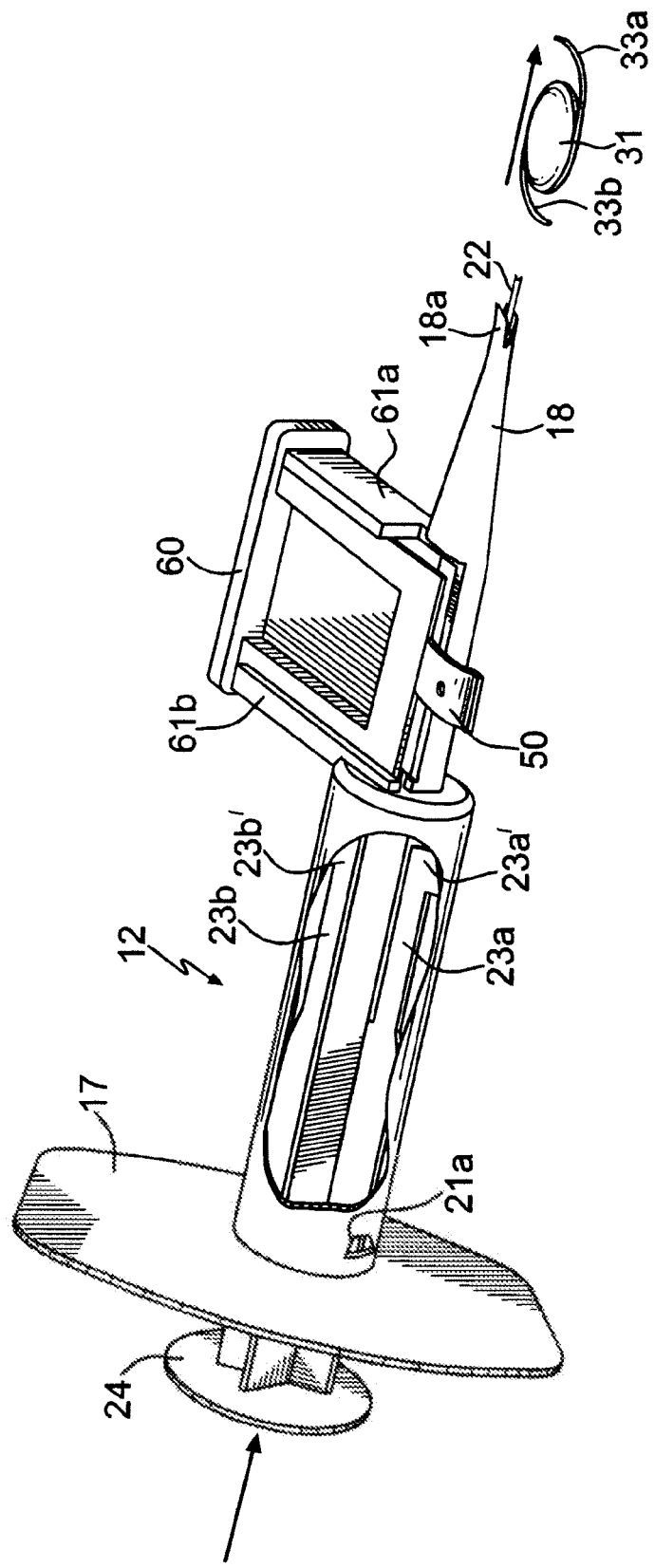
FIG. 7 is the view of FIG. 6 showing the IOL fully ejected from the injector device.

At this time, the haptic puller 80 is pulled away from the injector body 12 (FIG. 6) and the leading haptic 33a is straightened within injector tip 18. If desired or required, the plunger 20 may be advanced slightly prior to removing the haptic puller 80. The surgeon inserts the injector tip 18a into the incision cut into the eye and begins advancing the plunger 20. As the plunger 20 is advanced, the plunger tip 22 engages the optic periphery 31a and pushes IOL 30 forwardly with the trailing haptic 33b remaining located in recess 25 of plunger 20. Upon continued advancement of the plunger 20, the IOL 30 is pushed through the injector tip 18a and is finally expressed therefrom and into the eye (FIG. 7). A helical spring 27 may be provided about plunger shaft distal length 20a to provide increasing bias in the reverse direction as the plunger reaches the fully advanced position. This occurs as spring 27 is compressed between the leading edge 20b' of proximal shaft length 20b and the radial extension 12a of injector body 12 (see FIGS. 1 and 6). This assists the surgeon in maintaining precise control over plunger (and hence IOL) advancement and allows automatic retraction of the plunger upon relieving the pushing pressure being exerted against the plunger thumb press 24. This is useful for easily executing a second stroke of the plunger in order to engage and manipulate the trailing haptic into place in the eye. This feature, together with the bifurcated plunger tip 22, allows a more precise control and manipulation of the IOL with the plunger tip in-situ than would be possible with an injector device not having these features.

The Partially Preloaded Condition

Figure 10:
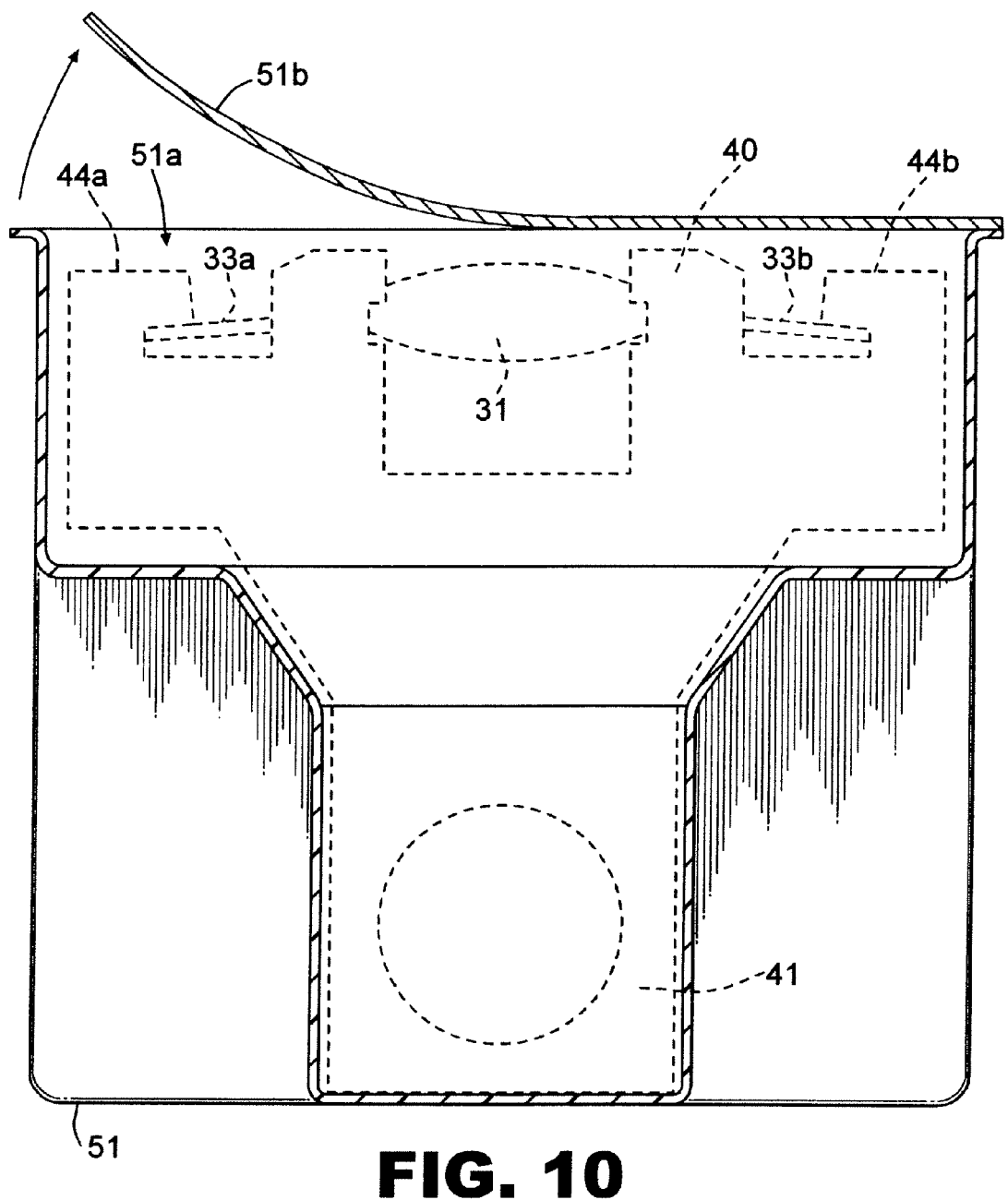
FIG. 10 is a side elevational view of the partially preloaded embodiment of the invention showing the retainer and IOL coupled together and sealed in a single package.

In an alternate embodiment of the invention, rather than being fully preloaded as described above, the injector device is "partially preloaded", meaning that the IOL 30 and retainer 40 are coupled together as shown in FIGS. 5A-C and sealed in a package 51 as shown in FIG. 10 which is separate from another package in which the injector body 12 is supplied. Package 51 may be thermoformed to include a cavity 51a in the general shape of retainer 40 and IOL 30 as coupled together. A flexible cover sheet 51b is sealed about the perimeter of cavity 51a to seal the retainer 40 and IOL 30 in package 51. This embodiment allows the doctor to choose a package having a retainer and specific IOL model therein. This is then combined with the separately packaged injector body 12 which is common to all IOL models. Thus, in this alternate embodiment, the doctor or nurse removes cover 51b to retrieve retainer 40 and IOL 30 therefrom. The injector body 12 is removed from its respective packaging and the retainer 40 having an IOL 30 already coupled thereto is attached to the injector body 12 at the time of surgery. It will be appreciated that direct handling and manipulation of the IOL 30 itself is not required in either the preloaded or partially preloaded embodiments of the invention.

In the partially preloaded embodiment, the injector body 12 is supplied with the compressor drawer 60 in the fully open position seen in FIG. 3B such that the stripper finger 50 is located laterally adjacent the opening 26 (or the stripper finger is not yet attached to the injector body 12 where the stripper finger is a separate component). The nurse or doctor then opens the package housing the inserter body and proceeds to couple the retainer and IOL to the injector body through opening 26. Once the retainer 40 and IOL 30 are coupled to the inserter body 12, the stripper finger 50 is inserted between the retainer wall surface 46 and IOL optic 31. This may be done by advancing the compressor drawer 60 to the mid-way position seen in FIGS. 1, 3A and 3C. In the embodiment shown in FIG. 3E, this is accomplished by attaching the stripper finger 50 and clip 50a combination to the injector body 12 opposite drawer 60.

FIGS. 13A-16A illustrate another preferred embodiment of the invention. For ease of understanding, the reference numerals used in the embodiments of previous FIGS. 1-12 will be used for similar parts found in FIGS. 13A-16B increased by 100. Unless stated otherwise, the description of other embodiments applies to this embodiment as well.

Referring to FIGS. 13A-13F, a retainer 140 for releasably holding an IOL is seen to include one or more, but preferably two optic support elements 142a and 142b each having a groove 142a', 142b' or other feature for releasably supporting the IOL optic 131 at the periphery 131a thereof. The grooves 142a', 142b' are spaced above the support surface 146 such that the optic 131 is likewise spaced above support surface 146. The distance between the support surface and optic is selected to enable the stripper finger 150 of the compressor drawer 160 to extend therebetween as explained more fully below. The upper surfaces 142a" and 142b" are slanted downwardly to provide a "lead-in" which facilitates positioning of the optic periphery 131a into gooves 142a', 142b'.

Alternatively, or in addition to the optic support elements, one or more, but preferably two haptic support elements 144a and 144b are provided on retainer 140, each of which include a groove 144a', 144b' or other feature for releasably supporting one or more, but preferably two haptics 133a and 133b which attach to and extend from the optic 131. The retainer 140 holds at least the IOL optic 131 in the unstressed state. It is furthermore preferable that retainer 140 hold the IOL haptics at the correct vault angle (i.e., the angle from which they normally extend from the IOL optic periphery). It is even furthermore preferable that the haptic support elements maintain loop haptics at the correct lens diameter $d_1$ (see FIG. 13G). In FIGS. 13A-D, it is seen that the haptic support elements 144a, 144b constrain the haptics 144a', 144b' along the outer curved edges thereof, respectively. This ensures that the lens diameter $d_1$, which is designed and set at manufacture, does not increase or bend out of specification during storage of the IOL and retainer.

Besides maintaining the lens diameter as described above, it is preferred that the optic 131 remain stationary with respect to the retainer 140 to prevent damage to the IOL and ensure proper alignment of the optic 131 with the opening 126 of the injector body 112 upon attaching the retainer to the injector body. As seen best in FIGS. 13A, B and D, a slot 143 is provided in at least one optic support element 142b wherein respective haptic 133b extends adjacent optic 131. Slot 143 acts to inhibit lateral translation or counter-clockwise rotation of IOL 130 (as viewed in FIGS. 13A and B) while coupled to retainer 140, particularly during shipping and storage thereof. Should the IOL 130 begin to translate or rotate counter-clockwise, haptic 133b will encounter and abut the side wall 143' defining the slot 143 and translation and rotation are thus inhibited. Likewise, translation or rotation of the IOL in the clock-wise direction is inhibited by the inside walls 142a", 142b" which the haptics will encounter and abut should they begin to translate or move in the clockwise direction.

With IOL 130 attached to the retainer 140, the retainer and IOL combination is ready to be attached to the injector device 112. As described above in relation to previous embodiments, this may be done at the time of manufacture, at the time of use by the surgeon or nurse, or any time therebetween.

Retainer 140 may further include first and second attachment legs. 145a, 145b extending from opposite edges of surface 146. Legs 145a and 145b are spaced apart a distance enabling retainer 140 to be removably attached to device 112 as seen in FIGS. 15A-15D by straddling drawer slides 161a, 161b which extend laterally from injector body 112 adjacent opening 126. Legs 145a, 145b may be provided with catches 145a', 145b' at the ends thereof to provide a snap-fit engagement between retainer 140 and drawer slides 161a, 161b, respectively. The snap-fit engagement should be strong enough to prevent unintentionally decoupling retainer 140 from body 112 yet also allow retainer 140 to be manually decoupled therefrom without the use of excessive force. As seen best in FIGS. 15A and 16A, first and second flanges 165a, 165b are provided at the junctures of drawer slides 161a, 161b and device body 112, respectively, and act to precisely locate legs 145a, 145b thereagainst and thus precisely locate retainer 140 on device body 112. Retainer 140 may further include first and second flanges 147a, 147b, which rest on drawer slides 161a, 161b when the retainer 140 is properly positioned on device body 112 as described above. Flanges 147a, 147b help stabilize retainer 140 on device body 112 and also aid the user in pivoting the retainer off the device about the flange corners 147a', 147b' which act as the pivot points (see also FIG. 15C).

Figure 13A:
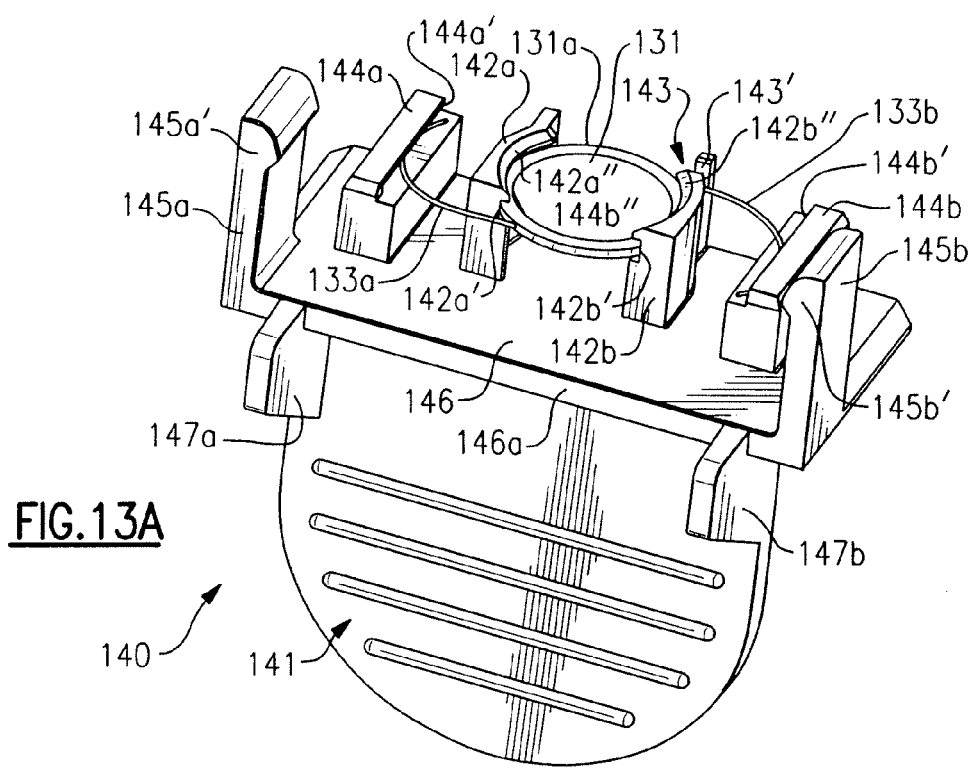
FIG. 13A is a perspective view of another embodiment of the lens retainer showing an IOL coupled thereto on the intended manner.
Figure 13C:
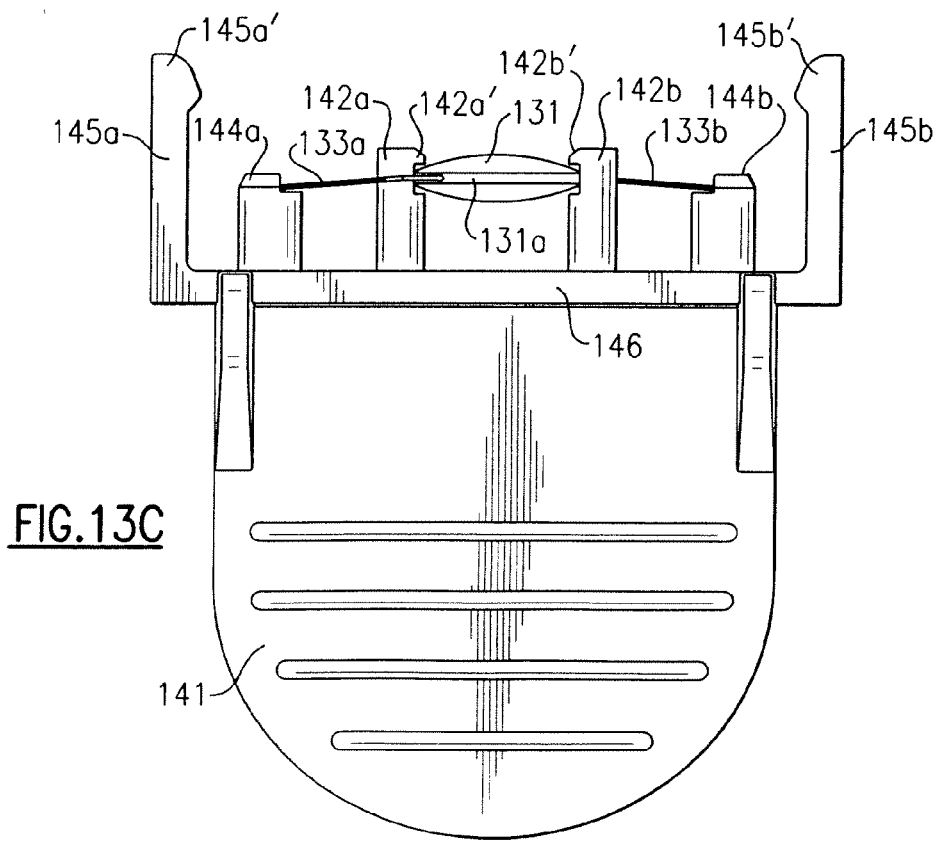
FIG. 13C is a side elevational view thereof.
Figure 13B:
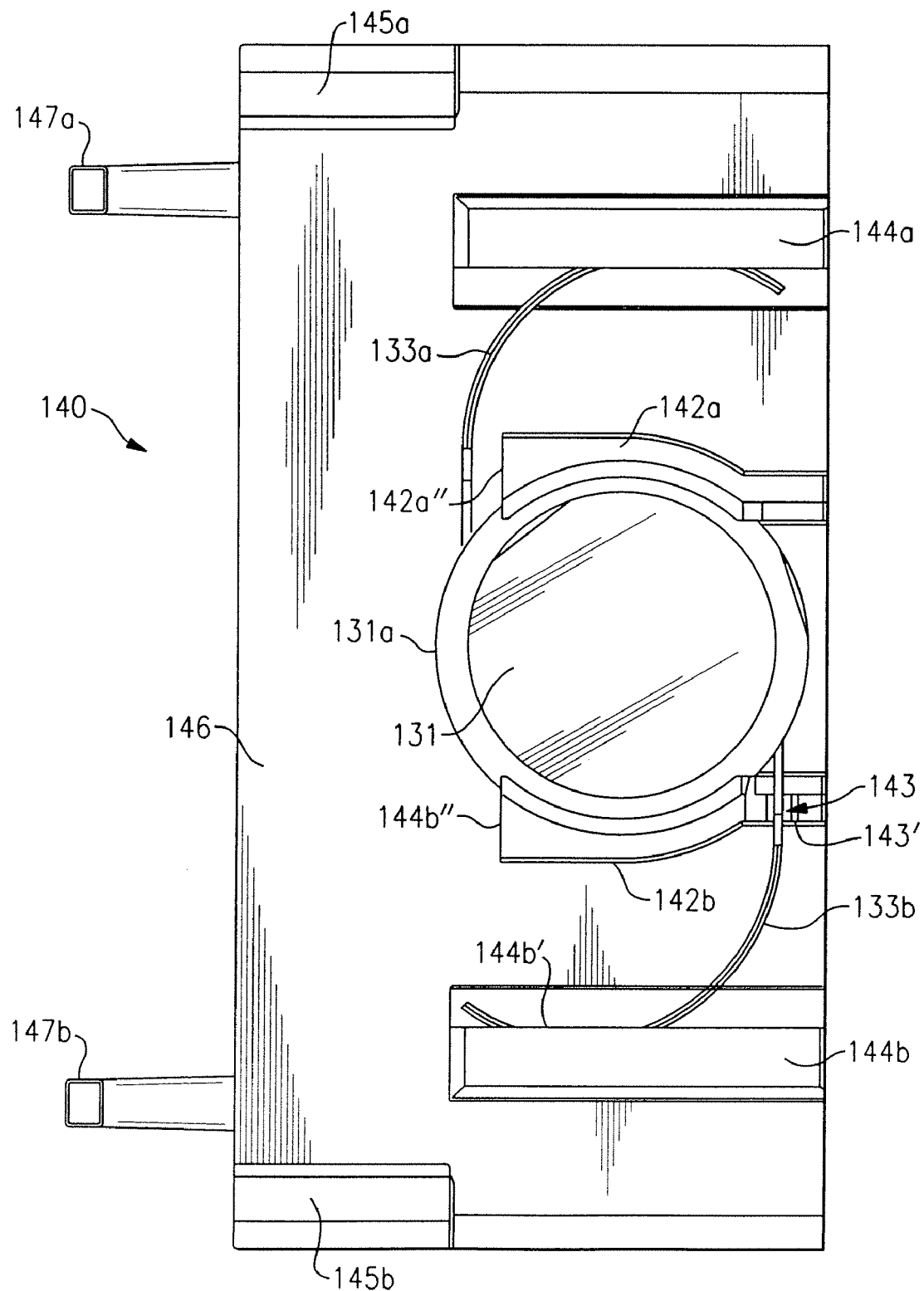
FIG. 13B is a top plan view of FIG. 13A.
Figure 13D:
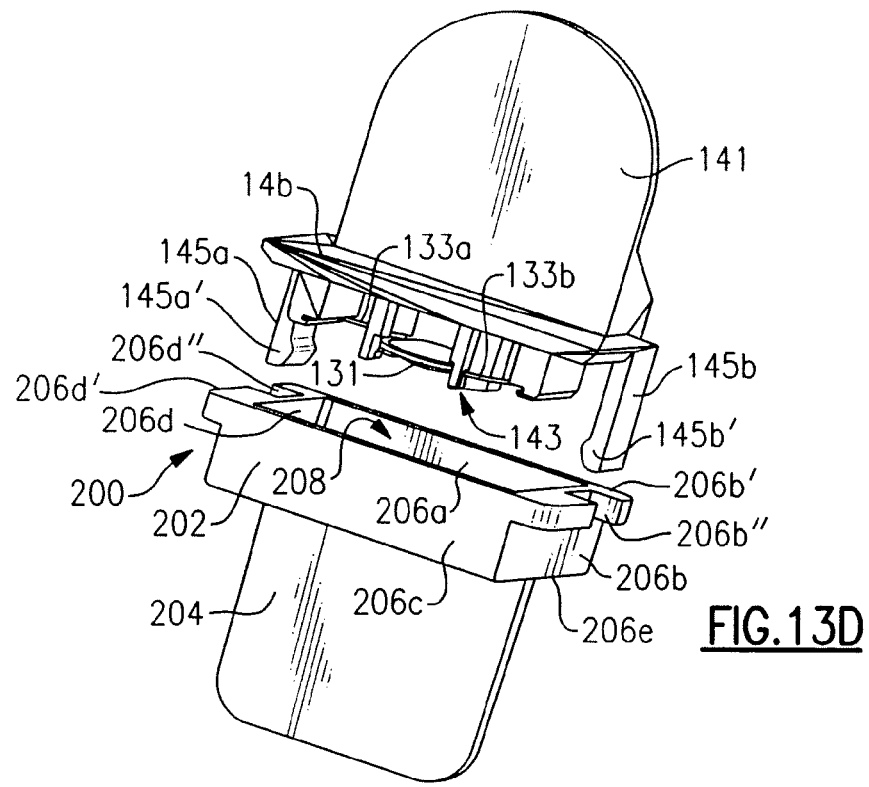
FIG. 13D is a perspective view of the retainer and IOL in spaced relation to a retainer cover.
Figure 13E:
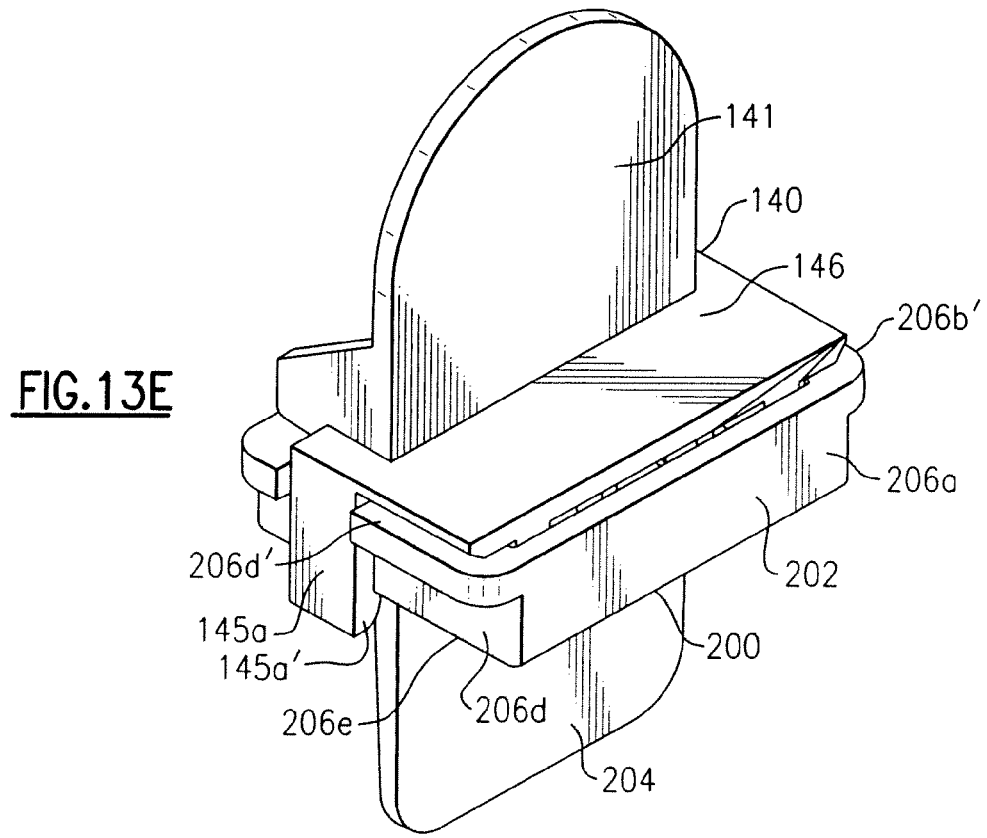
FIG. 13E is a perspective view showing the retainer and cover coupled together.
Figure 13F:
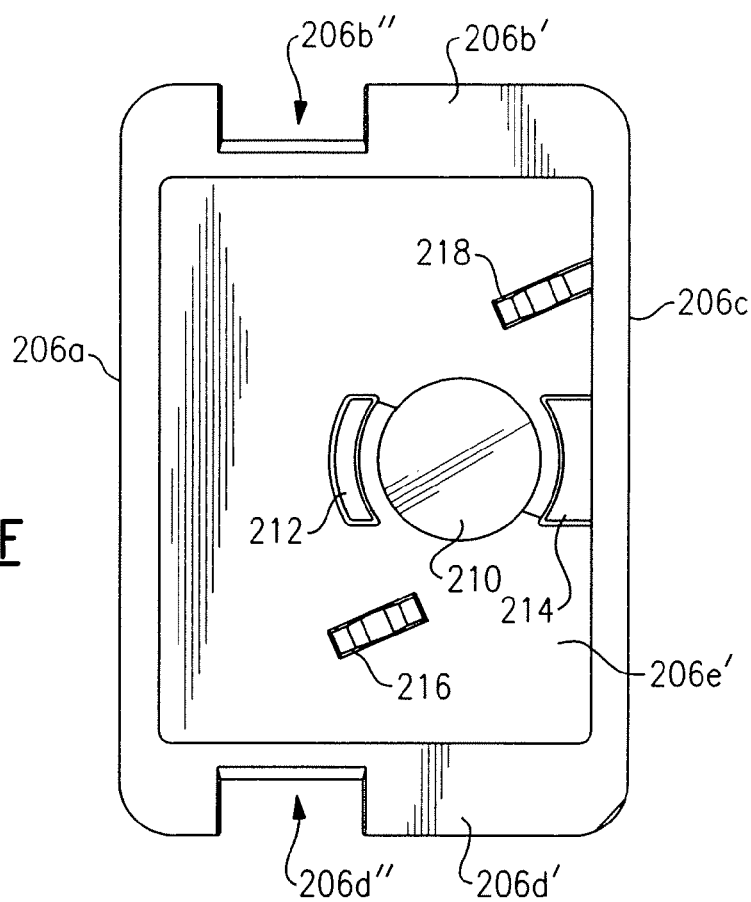
FIG. 13F is a bottom plan view of the retainer cover.
Figure 13G:
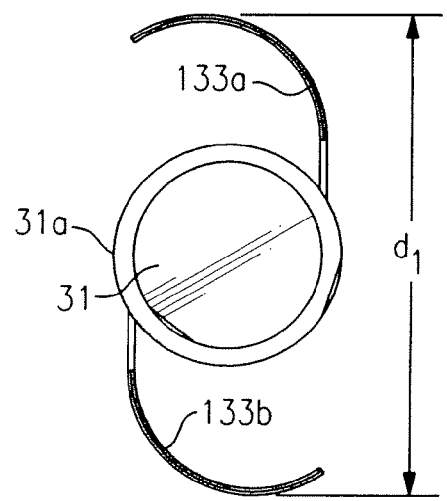
FIG. 13G is a plan view of a representative IOL for use with the present invention.

In the case where the retainer 140 is to be packaged and shipped separately of the injector 112, a protective cover 200 is provided which may be removably coupled to retainer 140 (FIGS. 13E-F). Cover 200 includes a finger grasp flange 204 extending from enclosure 202 having four side walls 206a, 206b, 206c and 206d and a top wall 206e all defining a central opening 208. Opposite side walls 206b and 206d each include a flange 206b', 206d' adjacent opening 208. Flanges 206b', 206d' each include a notch 206b", 206d" wherein the first and second attachment legs 145*a*, 145*b* of retainer 140 may freely slide, respectively. Thus, to initially attach the cover 200 to retainer 140, the two parts are aligned as seen in FIG. 13D and moved together until retainer surface 146 rests upon the flanges 206*b*', 206*d*' and catches 145*a*', 145*b*' engage top cover top wall 202*e* as seen in FIG. 13E. In the attached condition of the retainer and cover seen in FIG. 13E, the IOL optic 131 remains coupled to retainer 140. As seen in FIG. 13F, the interior of top wall 206*e*' may be provided with features to assist in providing clearance and/or support to the IOL. For example, a circular recess 210 may be provided which aligns with the position of IOL optic 131 to ensure there is enough clearance to prevent the IOL optic 131 from touching interior wall 206*e*'. One or more protrusions such as at 212 and 214 may also be provided to act as auxiliary supports for the optic peripheral edge 131*a*. One or more protrusions 218, 220 may be provided to act as auxiliary supports for haptics 133*a* and 133*b*, respectively. At the time of surgery, cover 200 is removed by pulling the retainer 140 away from the cover 200. The cover 200 may then be discarded.

Figure 14:
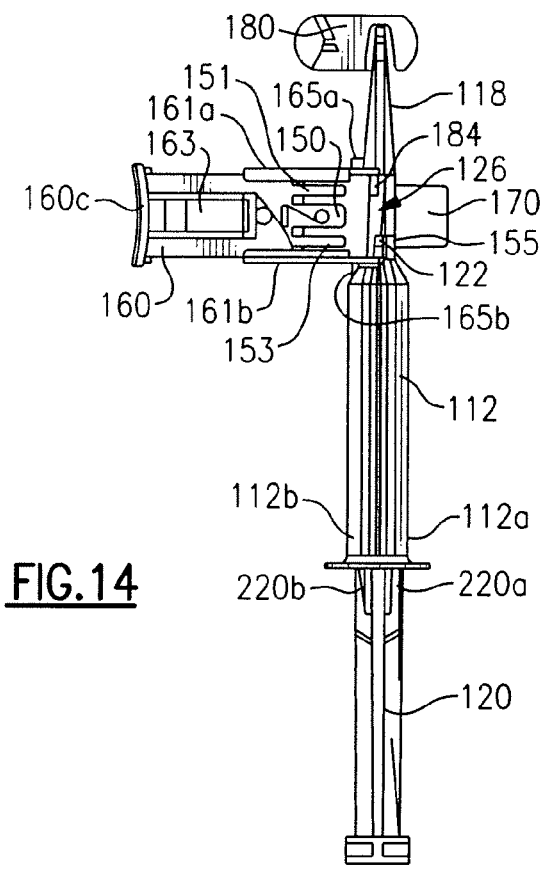
FIG. 14 is a plan view of another embodiment of the injector device with the compressor drawer shown in the fully open position relative to the injector body.
Figure 15A:
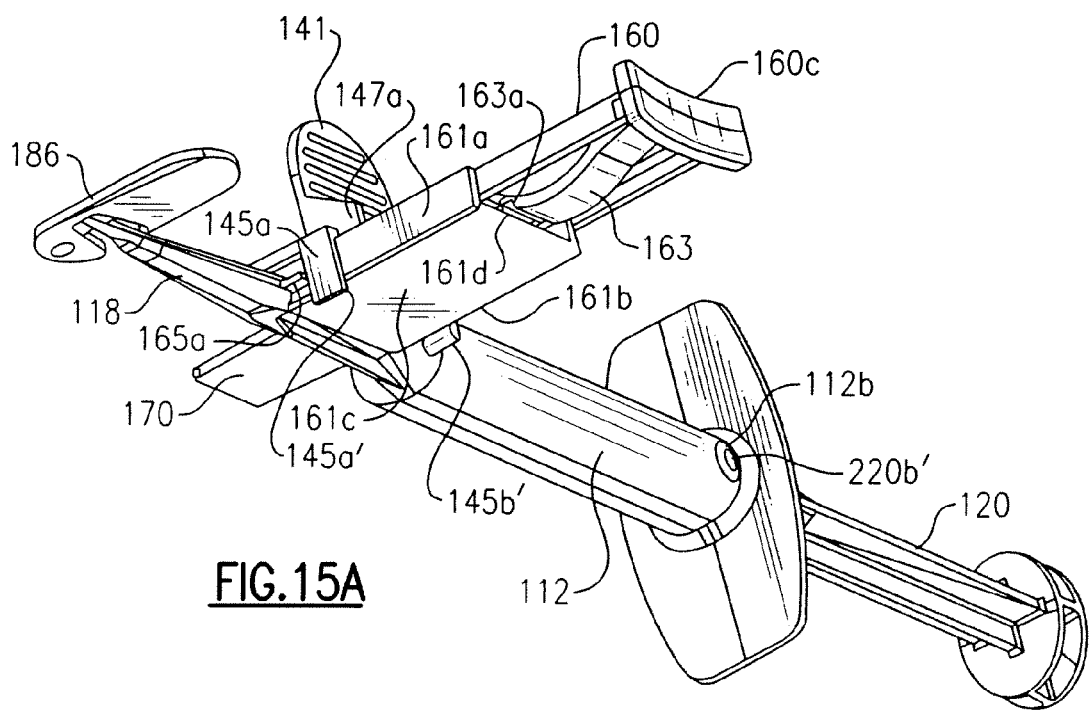
FIG. 15A is a perspective view of the injector device of FIG. 14.
Figure 15B:
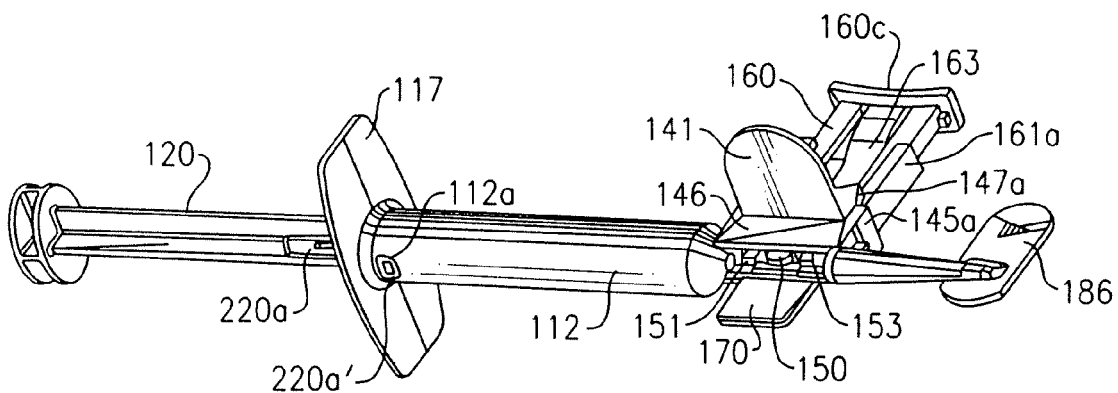
FIG. 15B is a perspective view of the injector device of FIGS. 14 and 15A showing the compressor drawer in the partly closed position relative to the injector body.
Figure 15C:
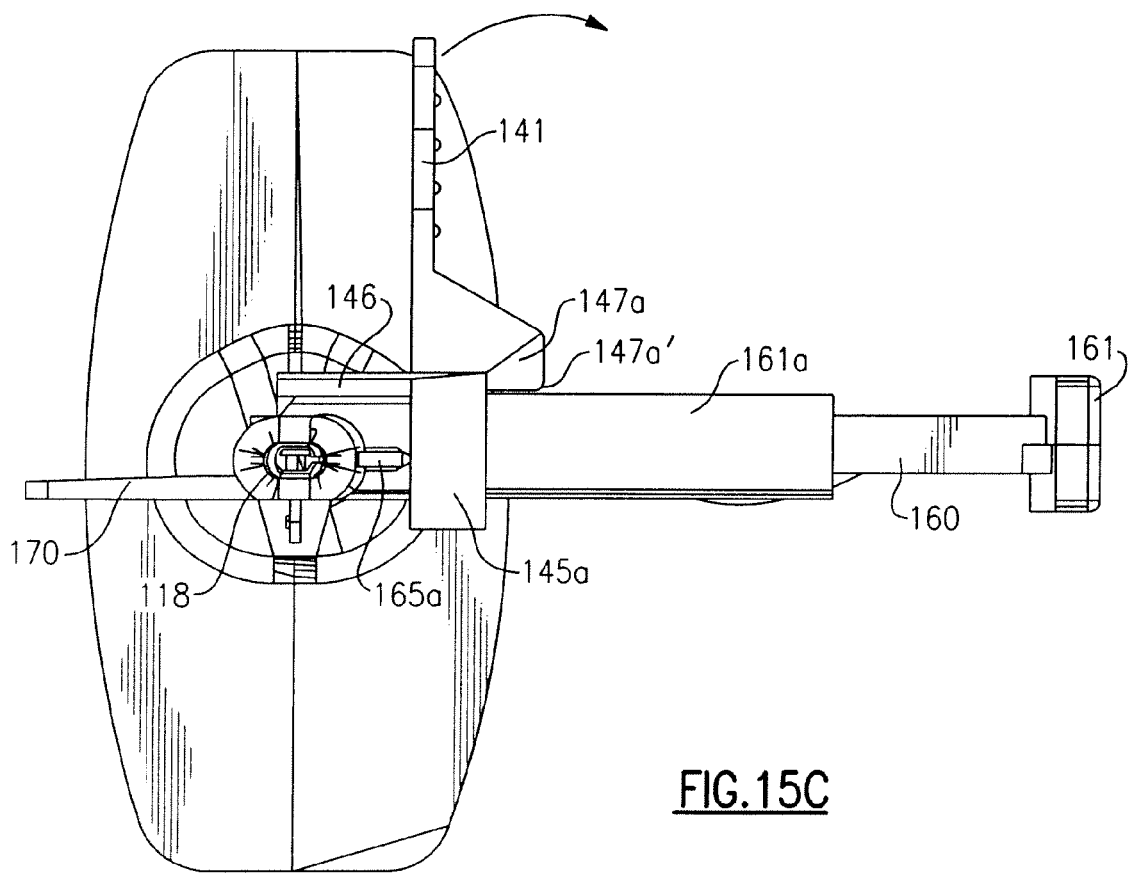
FIG. 15C is a front elevational view of FIG. 15B.
Figure 15D:
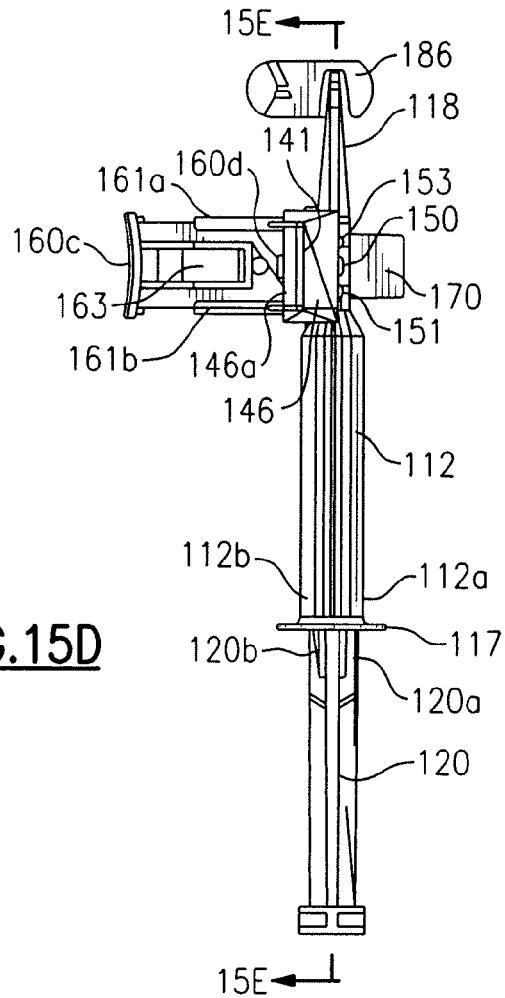
FIG. 15D is a top plan view of FIGS. 15B and 15C.
Figure 15E:
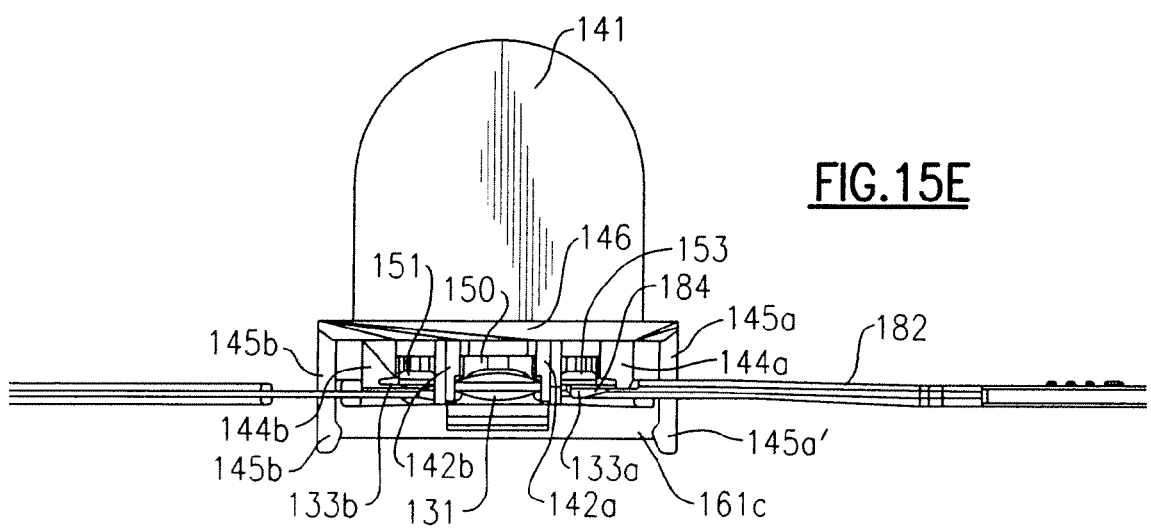
FIG. 15E is a side elevational view in cross-section of FIG. 15D showing the relative positioning of the retainer stripper fingers, IOL, plunger tip, and haptic puller when the compressor drawer is in the partly closed position.

Prior to attaching retainer 140 and IOL 130 combination to device 112, the compressor drawer 160 is set to the open position as seen in FIGS. 14 and 15A. The compressor drawer 160 includes opposite side rails 163*b*, 163*c* with a spring arm 161*c* extending therebwetween, a finger press 160*c*, an optic stripper finger 150 and first and second haptic stripper fingers 151 and 153 extending generally parallel to and spaced on either side of optic stripper finger 150. When in the open position, the leading edges of the optic and haptic stripper fingers 150, 151, 153 lie laterally spaced from opening 126 as seen best in FIG. 14. As seen best in FIG. 15A, the leading edge 163*a* of arm 163 has a groove which engages the leading edge 161*d* of shelf 161*c* to prevent unintended further advancement of drawer 160 with respect to device 112. This feature allows the open position of the drawer 160 to be correctly set at manufacturing and prevent premature advancement of the drawer during shipping and handling. With the drawer 160 in the open position, the retainer and IOL combination may be mounted thereto over opening 126 by grasping retainer 140 by finger grasp 141 and straddling legs 145*a*, 145*b* about drawer slides 161*a*, 161*b* as described above.

When it is time to use the device at surgery, the surgeon or nurse presses upon drawer finger press 160*c* while also pressing upward on arm 163 (e.g., with the thumb) to disengage the arm leading edge 163*a* from the shelf leading edge 161*d*. Once this is done, the drawer 160 is advanced further toward opening 126 of device 112 with arm 163 passing over shelf 161*c*. Advancement of the drawer is continued until stripper fingers 150, 151 and 153 have extended between the IOL 130 and retainer surface 146 as seen best in FIGS. 15B, 15D and 15E. This position will be realized by the user when vertically extending flange 160*d* of drawer 160 (see FIGS. 15D and 16B) abuts edge 146*a* of retainer surface 146 (see FIG. 15D).

Figure 15F:
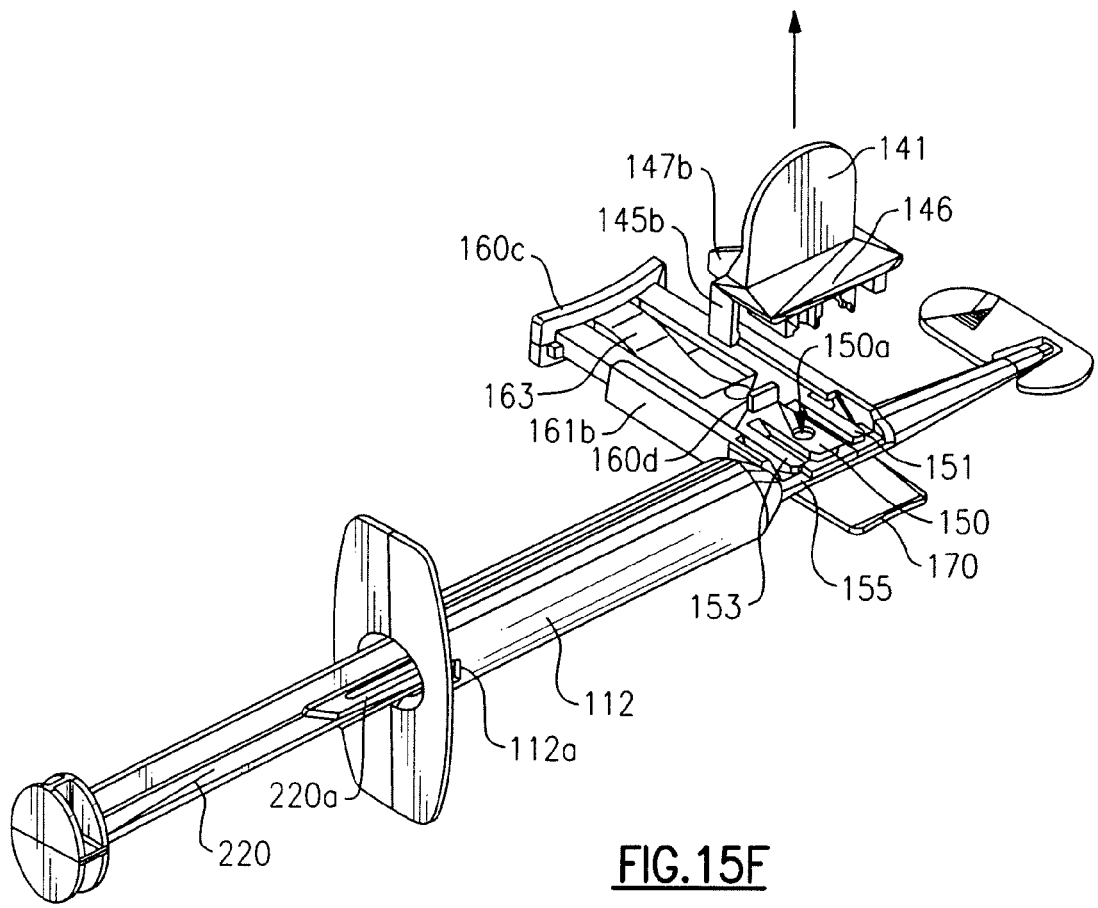
FIG. 15F is a perspective view of the injector device of FIGS. 14-15E showing the compressor drawer in the partly closed position and the retainer being removed from the injector device with the IOL remaining with the injector device.

With stripper fingers 150, 151 and 153 positioned between IOL 130 and retainer surface 126, retainer 140 may be decoupled from device 112 by grasping finger pull 141 and pulling away from the device 112 as seen in FIG. 15F. It is noted that the retainer 140 may be pulled straight (arrow in FIG. 15F) or in a pivoting movement (arrow in FIG. 15C) with respect to the device body 112. Prior to and/or after decoupling retainer 140, the surgeon may apply viscoelastic to the IOL 130 through opening 126 and/or opening 150*a*. It will be realized that central stripper finger 150 acts to strip the IOL optic 131 from retainer 140 while stripper fingers 151 and 153 act to strip respective haptics 133*a* and 133*b* therefrom.

Besides acting to strip the IOL from the retainer, the stripper fingers also assist in maintaining the IOL at least partly submerged in the viscoelastic puddle as applied by the surgeon. Without this assistance by the stripper fingers, the IOL may "float" on top of the viscoelastic which can be detrimental to a successful IOL delivery. It is also noted that the opening 150*a* in optic stripper finger 150 assists in stabilizing the IOL optic 31 as it is being stripped away from retainer 140. To explain, as retainer 140 is decoupled from injector body 112, the two haptics may release from their respective haaptic support elements at different times causing the optic to "tilt" in the direction of the haptic as it releases from its associated support element. Opening 150*a* thus assists in keeping the optic from tilting by providing a 360° surface against which the 360° peripheral edge 131*a* may press against during the stripping process. Opening 150*a*' may further be provided with an angled lead-in edge 150*a*' (FIG. 16C) to enhance this stabilizing effect.

Figure 16A:
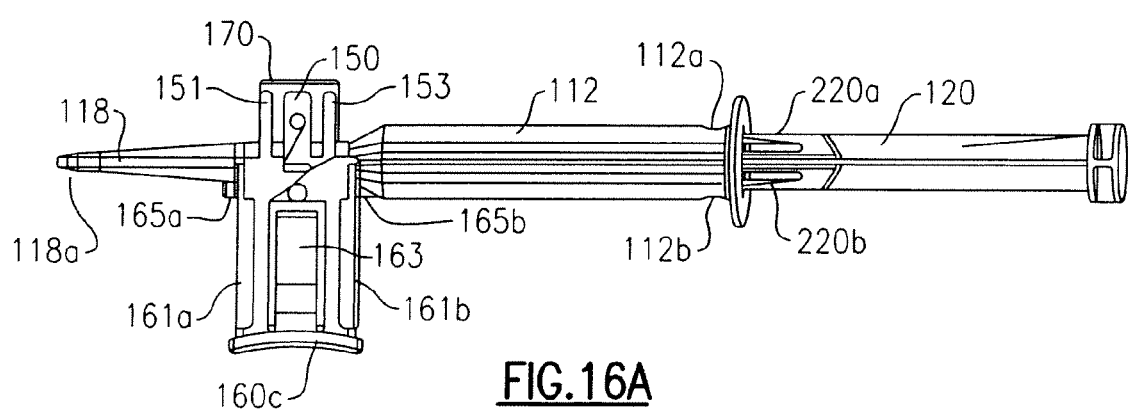
FIG. 16A is a top plan view of the injector device of FIGS. 14-15E following removal of the retainer and the compressor drawer moved to the fully closed position.
Figure 16B:
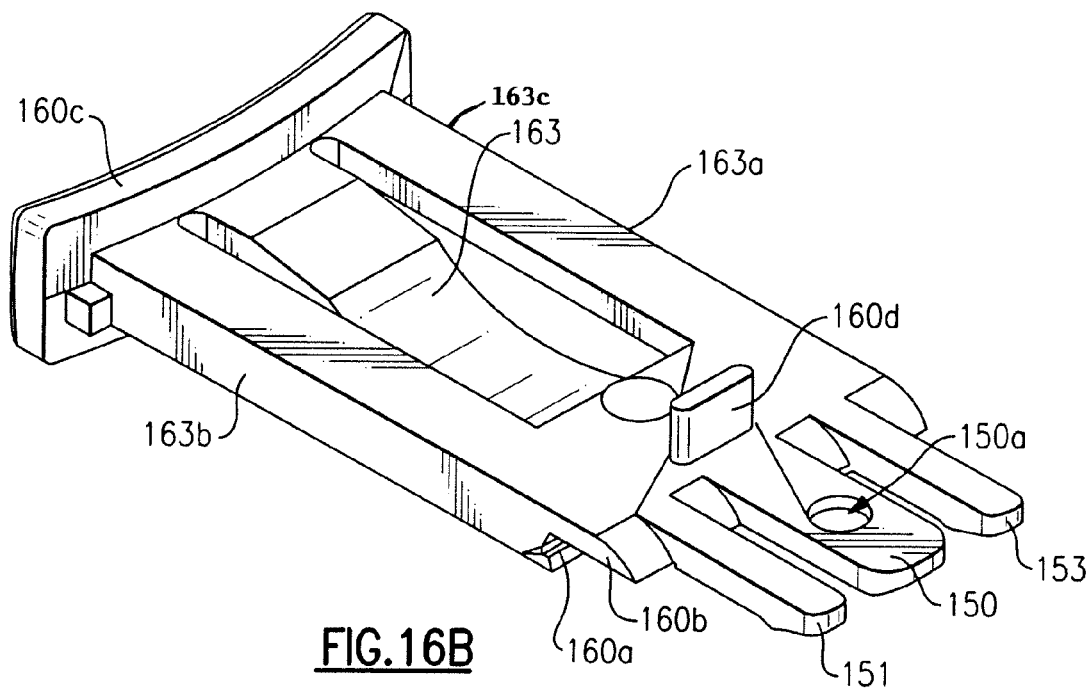
FIG. 16B is a perspective view of the compressor drawer of the embodiment of FIGS. 14-16A.
Figure 16C:
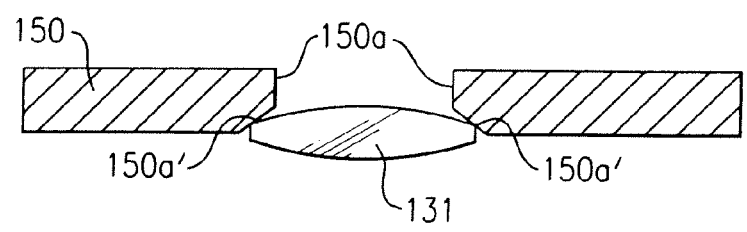
FIG. 16C is a cross-section view showing the IOL as it engages the through hole 150a of the optic stripper element 150 when the retainer is removed from the injector device.

Once retainer 140 is decoupled from the device, the IOL 130 is positioned in opening 126 in the manner described above (see FIG. 2A) and is ready for folding and delivery into an eye. The user thus proceeds by continuing to advance drawer 160 to the fully closed position by pressing inwardly on drawer finger press 160*c*. It is noted that a lateral opening 155 is provided in body 112 opposite drawer 60 (see FIGS. 14 and 15F). Opening 155 is provided to allow the free end of the trailing haptic 133*b* to pass therethrough should the closing of drawer 160 begin to pinch this haptic. A finger grasp 170 may be provided on device 112 opposite drawer 160 to help the user hold the device while closing the drawer. The fully closed position of drawer 160 is seen in FIG. 16A. In this position, stripper fingers 150, 151 and 153 are now located laterally of device 112 over flange 170. The IOL 130 is compressed and ready for delivery.

Figure 17:
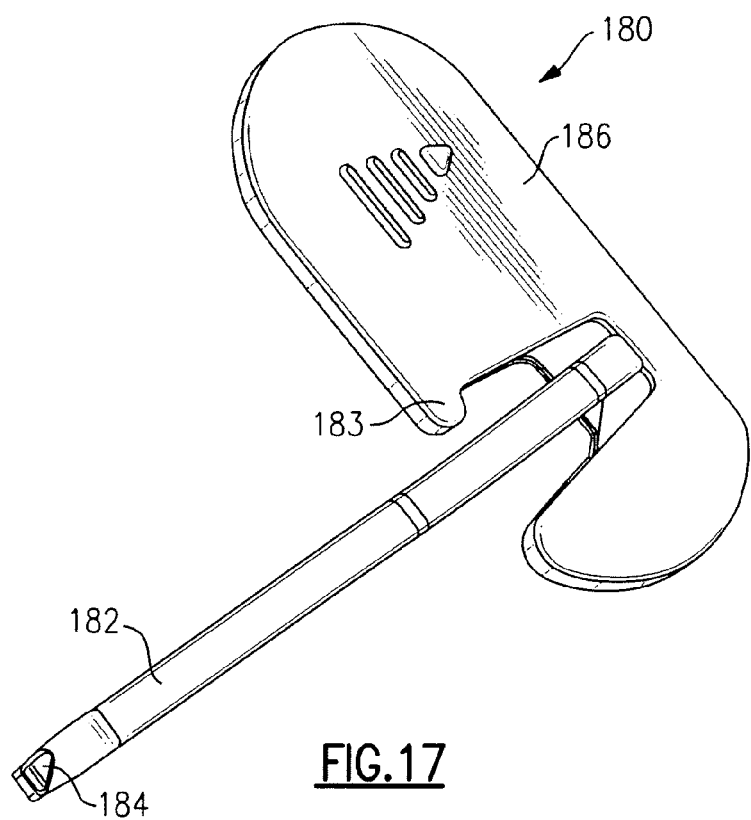
FIG. 17 is perspective view of another embodiment of the haptic puller component.

At this time, the haptic puller 180 is pulled away from the injector body 112 (see FIG. 6) and the leading haptic 133*a* is straightened within injector tip 118. As seen in FIG. 17, haptic puller 180 includes a finger pull 186 and a shaft 182 and tip 184. At assembly, the tip 184 is inserted into the injector tip with the finger pull located outwardly adjacent thereto (see FIG. 14). The tip 184 is configured with a lip to engage the leading haptic 133*a* (see FIG. 14 and 15E). At the time of use of device 110, the haptic puller 180 is grasped at finger pull 186 and pulled away from the injector body 112, thereby engaging and straightening the leading haptic 133*a* within tip 118, whereupon the haptic puller 180 may be discarded.

To ensure the leading haptic 133*a* becomes engaged with the haptic puller tip 184 when the IOL retainer 140 is removed from injector body 12, the haptic puller tip 184 is positioned in injector tip 118 in alignment with the leading haptic 133*a* as it is held by the haptic supporting element 144*a* of IOL retainer 140. Thus, upon detaching IOL retainer 140 from the injector body 112, the leading haptic 133*a* releases from the haptic supporting element 144*a* and falls into place on the haptic puller tip 184. A positioning nub 183 is formed on finger pull 186 and abuts the tip 118 when the haptic puller shaft 182 is fully inserted into the inserter tip 118. Nub 183 substantially inhibits lateral movement of the shaft 182 within tip 118 and thereby ensures proper and stable alignment of the haptic puller tip 184 with the retainer 140 and leading haptic 133*a* held thereby.

Figure 18:
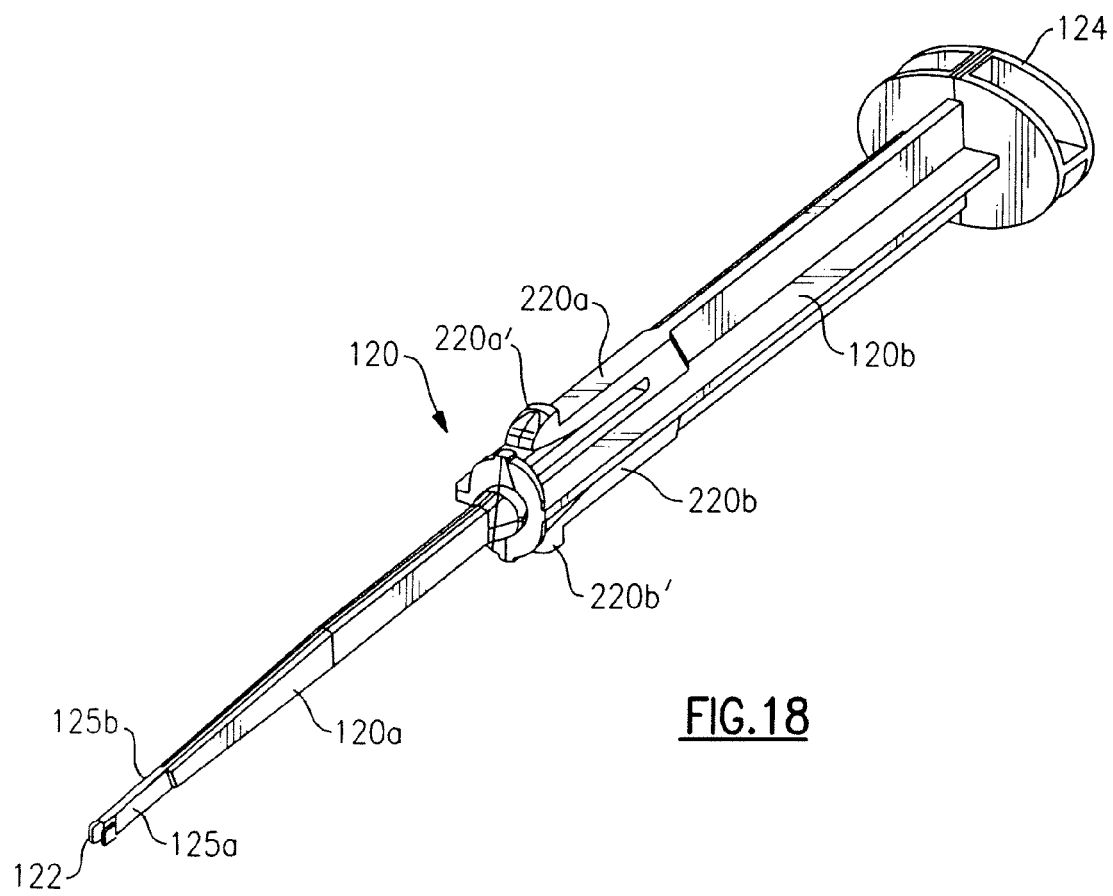
FIG. 18 is a perspective view of another embodiment of the plunger component.

If desired or required, the plunger 120 may be advanced slightly prior to removing the haptic puller 180. The surgeon inserts the injector tip 118*a* into the incision cut into the eye and begins advancing the plunger 120. As the plunger 120 is advanced, the plunger tip 122 engages the optic periphery 131*a* and pushes IOL 130 forwardly with the trailing haptic 133b locating in recess 125a of plunger 120. It is noted that plunger 120 may also include a recess 125b opposite recess 125a (see FIG. 18). Second recess 125b is provided so that if trailing haptic 133b fails to align with and become located in the first recess 125a, the trailing haptic will instead become located in the second recess 125b and thus have clearance to travel through and out the device lumen. Upon continued advancement of the plunger 120, the IOL 130 is pushed through the injector tip 118a and is finally expressed therefrom and into the eye.

A pair of spring springs 220a, 220b having respective tips 220a', 220b' may be provided on the plunger shaft. Injector body 112 may likewise be provided with a pair of through holes 112a, 112b wherethrough the tips may reside to set the initial (shipping) position of the plunger 120. These features are described more fully in our copending application Ser. No. 10/744,981 filed Dec. 22, 2003, incorporated herein by reference. Pressing the plunger causes the tips to retract out of holes 112a, 112b and thereafter provide bias against the interior of body 112. This assists the surgeon in maintaining precise control over plunger (and hence IOL) advancement. A spring (not shown) may also be provided about plunger shaft 120 to allow automatic retraction of the plunger upon relieving the pushing pressure being exerted against the plunger thumb press 24 as described above.

What is claimed is:

1. An injector device comprising:
   an injector body having a lumen extending longitudinally therethrough;
   an opening providing access to the lumen of said injector body;
   a retainer releasably holding an IOL comprising an optic, said retainer adapted to be removably attached to the injector body proximate said opening;
   a movable compressor drawer coupled to the injector body proximate the opening, the compressor drawer having an optic stripper element attached thereto,
   the optic stripper element adapted to extend between the retainer and the optic when the retainer is removably attached to the injector body wherein, when the retainer is removably attached to the injector body and the compressor drawer is in a partly closed position, the optic stripper element extends between the retainer and the optic, and when the retainer is removably attached to the injector body and the compressor drawer is in a fully open position, the optic stripper element does not extend between the retainer and the optic.

2. The injector device of claim 1, wherein said compressor drawer is moveable from a fully open position to a partly closed position and subsequently to a fully closed position with respect to said injector body.

3. The injector device of claim 2, wherein the compressor drawer further comprises a vertical flange, said flange abutting said retainer when said retainer is remobably attached to said injector body and when said compressor drawer is moved to said partly closed position, thereby preventing said compressor drawer from moving to said fully closed position until said retainer is removed from said injector device.

4. The injector device of claim 3 wherein said optic stripper element is configured such that upon removal of said retainer from said injector device, said IOL becomes located in said lumen of said injector device and is prevented from releasing with said retainer.

5. The injector device of claim 4 wherein said optic stripper element includes at least one through hole configured to engage the periphery of said IOL during removal of said retainer from said injector body.

6. The injector device of claim 2, wherein the compressor drawer is coupled to the injector body during each of the fully open position, the partly closed position and the fully closed positions.

7. The injector device of claim 1, wherein the IOL further comprises a first haptic and a second haptic, and wherein the compressor drawer further comprises a first and second haptic stripper elements that extend on either side of said optic stripper element, the first and second haptic stripper elements adapted to extend between the retainer and the first haptic of the IOL, and between the retainer and the second haptic of the IOL, respectively, when the retainer is removably attached to the injector body.

8. The injector device of claim 1 further comprising a finger grasp flange attached to said injector body opposite said compressor drawer to assist in manually handling said device.

9. The injector device of claim 1, wherein, when the optic stripper element is extended between the retainer and the optic and when the retainer is detached from the injector body, the IOL is detached from the retainer.

10. The injector device of claim 1, wherein the IOL has an optical axis and the compressor drawer is adapted to slide in a direction substantially perpendicular to the optical axis.

11. The injector device of claim 1, wherein the compressor drawer and the retainer are independently coupled to the injector body, such that the retainer can be detached from the injector without detaching the compressor drawer from the injector body.

12. The injector device of claim 2 wherein, when the retainer is removably attached to the injector body and the compressor drawer is in the partly closed position, the optic stripper element extends between the retainer and the optic, and when the retainer is removably attached to the injector body and the compressor drawer is in the fully open position, the optic stripper element does not extend between the retainer and the optic.

13. The injector device of claim 1, wherein the retainer is removably attached to the injector body.

14. The injector device of claim 13 wherein, when the compressor drawer is in the partly closed position, the optic stripper element extends between the retainer and the optic, and when the compressor drawer is in the fully open position, the optic stripper element does not extend between the retainer and the optic.

15. The injector device of claim 1, wherein said compressor drawer includes a spring arm having an edge configured to abut a feature of said injector device when said compressor drawer is in a partly closed position to prevent further closing of said compressor drawer until said edge is released from said feature of said injector device.

* * * * *